(12) United States Patent
Knuth et al.

(10) Patent No.: US 8,361,173 B2
(45) Date of Patent: Jan. 29, 2013

(54) FATTY ACID BLENDS AND USES THEREFOR

(75) Inventors: Mark Knuth, Poway, CA (US); Peter R. Beetham, Carlsbad, CA (US); Keith Walker, San Diego, CA (US); Greg F. W. Gocal, San Diego, CA (US)

(73) Assignee: Nucelis Inc., San Diego, CA (US)

( * ) Notice: Subject to any disclaimer, the term of this patent is extended or adjusted under 35 U.S.C. 154(b) by 0 days.

(21) Appl. No.: 13/227,437

(22) Filed: Sep. 7, 2011

(65) Prior Publication Data

US 2012/0073186 A1    Mar. 29, 2012

Related U.S. Application Data

(62) Division of application No. 12/306,477, filed as application No. PCT/US2007/015017 on Jun. 27, 2007, now Pat. No. 8,029,579.

(60) Provisional application No. 60/817,558, filed on Jun. 28, 2006.

(51) Int. Cl.
    *C10L 1/18*      (2006.01)

(52) U.S. Cl. .............................. 44/385; 562/606; 554/1

(58) Field of Classification Search .................... 44/385; 562/606; 554/1
See application file for complete search history.

(56) References Cited

U.S. PATENT DOCUMENTS

| | | | |
|---|---|---|---|
| 3,541,723 A * | 11/1970 | Eckert .............................. | 44/385 |
| 3,849,457 A * | 11/1974 | Haag et al. ........................ | 560/8 |
| 4,364,743 A | 12/1982 | Erner | |
| 4,945,050 A | 7/1990 | Sanford et al. | |
| 5,100,792 A | 3/1992 | Sanford et al. | |
| 5,204,253 A | 4/1993 | Sanford et al. | |
| 5,298,421 A | 3/1994 | Davies et al. | |
| 5,302,523 A | 4/1994 | Coffee et al. | |
| 5,334,711 A | 8/1994 | Sproat et al. | |
| 5,378,249 A | 1/1995 | Morrison | |
| 5,389,113 A | 2/1995 | Demmering et al. | |
| 5,455,167 A | 10/1995 | Voelker et al. | |
| 5,512,482 A | 4/1996 | Voelker et al. | |
| 5,565,350 A | 10/1996 | Kmiec | |
| 5,667,997 A | 9/1997 | Voelker et al. | |
| 5,730,029 A | 3/1998 | Stoldt et al. | |
| 5,731,181 A | 3/1998 | Kmiec | |
| 5,756,325 A | 5/1998 | Kmiec | |
| 5,760,012 A | 6/1998 | Kmiec et al. | |
| 5,780,296 A | 7/1998 | Holloman et al. | |
| 5,795,972 A | 8/1998 | Kmiec | |
| 5,871,984 A | 2/1999 | Kmiec | |
| 5,888,983 A | 3/1999 | Kmiec et al. | |
| 5,945,339 A | 8/1999 | Holloman et al. | |
| 5,955,329 A | 9/1999 | Yuan et al. | |
| 6,004,804 A | 12/1999 | Kumar et al. | |
| 6,010,907 A | 1/2000 | Kmiec et al. | |
| 6,129,772 A * | 10/2000 | Weers et al. ..................... | 44/385 |
| 6,150,512 A | 11/2000 | Yuan | |
| 6,271,360 B1 | 8/2001 | Metz et al. | |
| 6,461,393 B1 * | 10/2002 | Krull et al. ....................... | 44/385 |
| 6,479,292 B1 | 11/2002 | Metz et al. | |
| 6,660,849 B1 | 12/2003 | Dehesh | |
| 7,060,500 B2 | 6/2006 | Metz et al. | |
| 2004/0006792 A1 | 1/2004 | Fillatti et al. | |
| 2005/0085653 A1 | 4/2005 | Garro et al. | |
| 2006/0026963 A1 | 2/2006 | Adibhatla | |

FOREIGN PATENT DOCUMENTS

| | | |
|---|---|---|
| EP | 0 626 387 | 11/1994 |
| EP | 0 679 657 | 11/1995 |
| EP | 0 969 014 | 1/2000 |
| WO | WO-92/01370 | 2/1992 |
| WO | WO-98/49350 | 11/1998 |
| WO | WO-99/07865 | 2/1999 |
| WO | WO-99/40789 | 8/1999 |
| WO | WO-99/58702 | 11/1999 |
| WO | WO-99/58723 | 11/1999 |
| WO | WO-01/15740 | 3/2001 |
| WO | WO 2004/006792 A1 | 1/2004 |
| WO | WO-2008/123847 | 10/2008 |

OTHER PUBLICATIONS

International Search Report dated Sep. 26, 2008 for PCT International Patent Application No. PCT/US2007/015017.
Byung et al., "Chemical and Physical properties of Butterfat-Vegetable oil Blend spread Prepared with Enzymatically Transesterified Canola Oil and Caprylic Acid" J. Agric Food Chem., 53: pp. 4954-4961, (2005).
Young et al., Interchangeability of fats and oils. JAOCS, 62(2), pp. 372-376 (1985).
Communication pursuant to Article 94(3) EPC dated Dec. 1, 2011 for EPO Patent Application No. 07809993.4.
Ag, Innovation News, vol. 12, No. 3; Jul.-Sep. 2003.
Cahoon and Shanklin, Substrate-dependent mutant complementation to select fatty acid desaturase variants for metabolic engineering of plant seed oil. Proc. Nat. Acad. Sci. 97(22): 12350-12355, 2000.
Carlsson, et al, A KAS2 cDNA complements the phenotypes of the *Arabidopsis* fab1 mutatnt that differs in a single residue bordering the substrate binding pocket, Plant Journal, (2002), (29)6:761-770.
Dehesh, et al, Production of high levels of 8:0 and 10:0 fatty acids in transgenic canola by overexpression of Ch FatB2, a thioesterase cDNA from *Cuphea hookeriana*, Plant J, (1996), 9(2):167-172.
Dittmar, et al, Production of standardized biodiesel, Erdoel Erdgas Kohle, (2003), 119(10):356-362.
Eccleston, et al, Expression of lauroyl-acyl carrier protein thioesterase in *Brassica napus* seeds induces pathways for both fatty acid oxidation and biosynthesis and implies a set point for triacylglycerol accumulation, Plant Cell, (1998), 10(4):613-621.

(Continued)

*Primary Examiner* — Cephia D Toomer
(74) *Attorney, Agent, or Firm* — Michael A. Whittaker; Acuity Law Group, P.C.

(57) ABSTRACT

Provided herein are blends oils or fatty acids comprising more than 50% medium chain fatty acids, or the fatty acid alkyl esters thereof, and having low melting points. Such blends are useful as a fuel or as a starting material for the production of, for example, a biodiesel. Also provided genetically altered or modified plants, modified such that the amount of medium chain fatty acids generated by the plant are increased. Further provided is a method of predicting the melting point of a blend of fatty acid methyl esters and the use of such a method for identifying blends suitable for use as, for example, a biodiesel.

12 Claims, 6 Drawing Sheets

OTHER PUBLICATIONS

Frame et al., Production of fertile transgenic maize plants by silicon carbide whisker-mediated transformation, Plant Journal 6:941-948, 1994.

Gallois et al., Leaf Disk Transformation Using Agrobacterium tumefaciens-Expression of Heterologous Genes in Tobacco, Methods in Molecular Biology, 55:89-107, 1996.

Geller et al., Rapid Screening of Biologically Modified Vegetable Oils for Fuel Performance, Transactions of the American Society of Agricultural Engineers 42(4):859-862, 1999.

Geller, et al, Fuel properties of oil from genitically altered *Cuphea viscosissima*, Indust Crops Prod, (199), 9(2):85-91.

Goodrum et al., Physical Properties of Low Molecular Weight Triglycerides for the Development of Bio-Diesel Fuel Models, Bioresource Technology, 56:55-60, 1996.

Graboski, et al., Combustion of Fat and Vegetable Oil Derived Fuels in Diesel Engines, Prog.Energy Combustion Sci., 24: 125-164, 1998.

Kinney et al., Modifying soybean oil for enhanced performance in biodiesel blends, Fuel Processing Technology, 86:1137-1147, 2005.

Kipp et al., Gene Targeting in Plants via Site-Directed Mutagenesis, Methods in Molecular Biology 133:213-221, 1999.

Knapp, et al, Modifying the seed storage of lipids of *Cuphea*: A source of medium chain triglycerides, Seed Oils for the Future, 14:143-154.

Knothe et al., Biodiesel: The Use of Vegetable Oils and Their Derivatives as Alternative Diesel Fuels, published on-line at www.biodiesel.org/resources/reportsdatabase/reports/gen/19961201_gen-162.pdf.

Knothe, G., Dependence of biodiesel fuel properties on the structure of fatty acid alkyl esters, Fuel Processing Technology, 86:1059-1070, 2005.

Mittelbach, M., Diesel Fuel Derived from Vegetable Oils, VI: Specifications and Quality Control of Biodiesel, Bioresource Technology, 56:7-11, 1996.

Phippen, et al, Total seed oil and fatty acid methyl ester contents of *Cuphea* accessions, Indust Crops Products, (2004), 24(1):52-59.

Stournas et al., Effects of Fatty Acid Derivatives on the Ignition Quality and Cold Flow of Diesel Fuel, JACOS, 72:433-437, 1995.

Supelco 18919: Lipid Standards: Fatty Acid Methyl Ester Mixtures C:4-C24:1, Sigma Aldrich Catalog 2011.

Supplementary European Search Report in application EP 07809993 dated Sep. 15, 2010.

US Notice of Allowance for U.S. Appl. No. 12/306,477 dated Jun. 24, 2011.

US Office Action for U.S. Appl. No. 12/306,477 dated Jan. 19, 2011.

Preliminary Opinion in related Ukraine Patent Application No. a2009 00631, dated Nov. 2, 2011.

Office Action in related Ukraine Patent Application No. a2009 00631, dated Mar. 2, 2012.

\* cited by examiner

```
  1  MVATSATSSF FPLPSFPLDP TAKTNKVTTS TNFSGLSPTP NSSGRMKVKP
 51  NAXAPPKING KRVGLPSGSV KPDNETSSQH PAAPRTFINQ LPDWSMLLAA
101  ITTVFKAAEK QWMMLDWKPR RSDVIMDPKG LGRIVXDGLV FRQNFSIRSY
151  EIGADRSASI ETVMNHLQET ALNHVKTAGL LGDGXGSTPE MVKKNLIWVV
201  TRMQVVVDKY PTWGDVVEVD TWVSQSGKNG MRRDWLVRDG NTGEILTRAS
251  SVWVMMNKLT RRLSKIPEEV RGEIEPYFVN SDFVLAEDSR KLTKLDDKTA
301  DYVRSGLTPR WSDLDVNQHV NNVKYIGWIL ESAPVGMMES QKLKSMTLEY
351  RKECGR    (SEQ ID NO:1)
```

FIG. 1

```
  1  MVATSATSSF FPVPSSSLDP NGKQNKIGST NLAGLNSAPN SGRMKVKPNA
 51  QAPFKINGKK VGLPGSVDIV RTDTETSSHP APRTPINQLP DWSMLLAAIT
101  TIFLAAEKQW MMLDWKPRRS DMLVDPFGIG RIVQDGLVFR QNFSIRSYEI
151  GADRSASIET VMNHLQETAL NHVKTAGLLG DGPGSTPEMF KKNLIWVVTR
201  MQVVVDKYPT WGDVVEVDTW VSQSGKNGMR RDWLVRDCNT GETLTRASSV
251  WVMMNKLTRR LSKIPEEVRG EIEPYFVNSD PVLAEDSRKL TKIDDKTADY
301  VRSGLTPRWS DLDVNQHVNN VKYIGWILES APVGIMERQK LKSMTLEYRR
351  ECGRDSVLQS LTAVTGCDIG NLATAGDVEC QHLLRLQDGA EVVRGRTEWS
401  SKTPTTTWGT AP  (SEQ ID NO:2)
```

AAL24309 *Arabidopsis thaliana* PTR

FIG. 2

```
  1 MVGASSSYAS PLCTNFVAAC NSVSHGGGDS RQAVALQSGG RSRRRKQLSK CSVASSSASI
 61 QALVTSCLDF GPCTHYNNNN ALSSLFGGNS VSLSRNQRRL NRAASSGGAM AVMEMEEEAA
121 VNKKPPTEQR RVVVTGMGVE TSLGHDPHIF YENLLQGNSG ISQIENFDCS EFPTRIAGEI
181 KSFSTEGWVA PKLSKRMDRF MLYLLTAGKK ALADGGVTDE VMAEFDKTKC GVLIGSAMGG
241 MKVFYDAIEA LRISYKKNNP FCVPFATTNM GSAMLANDLG NMGPNYSIST ACATSNFCIL
301 NSANRIIKSG ADVNLCGGSD AVIIPIGLGG FVACRALSQR NNDPTKASRP WDTRRDGFVM
361 GEGAGVLLLE ELEHAKKRGA TIYAEFLGGS FTCDAYHMTE PEPDGAGVIL CIERALASAG
421 ISKEQINYIN AHATSTHAGD IKEYQALARC FGQNPELKVN STKSMIGHLL GAAGAVEAVA
481 TVQAIRTGWV HPNINLENPD SGVDTKLLVG PKKERLQIKA ALSNSFGFGG HNSSIIFAPY
541 K  (SEQ ID NO:3)
```

Arabidopsis thaliana KAS II (NP_849888) Amino acid sequence

FIG. 3

```
   1 ATTTGTATAG TGTTGTATCT CTCTCTCTCT CTCTCTGTCT GTTTGTTTCA GAGAAGGATT
  61 TTTGGCGTCT CCACGCACGA TTTAACGCAT CGAAGCTCTC TGCACGCTTC CTGAAAGAGA
 121 GAGAGAAGAG AGAGATCGCA GATCGATTTC TCTTAAATCT CTCGTGAATC CCATTTGCCT
 181 TCTCCTGCT AGATTCTCTC TTCTTCTCTT CACCCATTTC TCGCTTCTC CTTTGTTCTC
 241 TCACTGGGT TCTTCTCAAA GCTTCTTCCT TTTTATGCCA TGGTGGGTGC GTCTTCCTCT
 301 TACGCATCTC CGTTATGTAC CTGGTTTGTT GCTGCTTGCA TGTCCGTCTC TCACGGTGGA
 361 GGAGATAGCC GTCAGGCTGT TGCTCTTCAA TCTGGTGGGC GGATCGGCA AGGAGGCAG
 421 CTTAGCAAAT GCTCTGTCGC TTCTGGATCC GCTAGCATTC AGGCTCTCGT CACTTCTTGT
 481 TGGATTTTG GTCCTTGTAC TCACTACAAC AACAACAATG CATTGTCTTC TCTCTTTGA
 541 TCGAATAGTG TTTCTTTGAA TCGAAACCAG AGGAGATTGA ATCGTGCTGG TAGCTCGGGT
 601 GGAGCCATGG CAGTGATGGA GATGGAAAAG GAAGCTGCGG TTAACAAGAA ACCACCTACG
 661 GAGCAGCGTC GAGTTGTAGT GACAGGCATG GGAGTTGAAA CATCATTGGG TCATGACCCA
 721 CATACCTTCT ATGAGAATTT GCTACAAGGC AACAGTGGTA TAGCCAGAT TGAAAATTTT
 781 GATTGTTCTG AATTTCCTAC GCGAATTGCG GGAGAGATCA AAGCTTCTC GACTGAAGGA
 841 TGGGTTGCTC CAAAACTTTC TAAAGGATG GACAAATTCA TGCTCTATCT TCTCACAGCT
 901 GGTAAGAAAG CTTTGGCTGA TGGTGGGGTT ACTGATGAAG TAATGGCAGA GTTTGACAAA
 961 ACCAAATGTG GAGTTTTGAT TGGCTCGGCA ATGGGAGGA TGAAGGTCTT TTACGATGCT
1021 ATTGAAGCTC TGAGAATCTC TTACAAGAAG ATGAATCCTT TTTGTGTACC TTTTGCGACA
1081 ACAAACATGG GTTCTGCTAT GCTTGCCATG GATCTGGGAT GGATGGGCCC AAACTATTCT
1141 ATTCAACTG CTTGTGCCAC AAGCAACTTT TGCATTCTGA ATTCAGCAAA CCACATTATT
1201 AAAGGTGAAG CTGATGTAAT GCTCTGTGGG GGCTCAGATG CAGTTATTAT TCCAATAGGG
1261 TTGGGAGGTT TTGTTGCATG CCGGGCTCTT TCACAAAGGA ATAATGATCC CACAAAAGCT
1321 TCACGTCCTT GGGATACCAA TCGAGATGGT TTCGTGATGG GAGAGGGAGC TGGAGTTCTA
1381 CTTTGGAAG AACTCGAGCA TGCTAAGAAA AGAGGTGCAA CTATCTACGG AGAGTTCCTC
1441 GGTGGGAGTT TCACATGTGA TGCCTATCAC ATGACCGAGC CTCACCCTGA TGGGGCTGGT
1501 GTTATTCTCT GTATTGAGAG AGCGTTAGCT AGTGCTGGGA TTTCCAAGGA ACAAATAAAT
1561 TACATAAATG CACATGCAAC CTCAACGCAT GCTGGAGATA TAAGGAATA CCAAGCCTT
1621 GCTCACTGTT TTGGCCAAAA TCCTGAGCTT AAGGTAAATT CCACAAAATC TATGATTGGA
1681 CACTTGCTGG GAGCTGCTGG GGCCGTGGAG GCTGTTGCAA CTGTGCAGGC GATACGGACC
1741 GGATGGGTTC ATCCAAATAT CAACCTCGAG AATCCAGACA GTGGAGTGGA TACAAAGCTG
1801 CTGGTGGGTC CTAAGAAGGA GAGACTGGAC ATTAAAGCAG CCTTGTCAAA TTCATTCGGG
1861 TTTGGTGGTC ATAACTCCAG CATCATTTTT GCTCCTTACA ACTGAAAGCC AAAGCAGTTG
1921 CTTGTACTCC AAACCTGATT GTATAACTTG CTGTAAGTGT TTTACAAGAA GTTCCCATG
1981 TTATGCTAGT GTTACGTCGA GGGAATCAAC AGAGTTTGTT CAACTACCAA GAGCTAAGCT
2041 AAGTTTCTTA GGATCAAGAT CTGATGAGCC AAAGACTTGG ACAGGAGCTA AAACGTGCTA
2101 GAGAATCAG AGTTTGGATT CGCCATTAAA ATTCTGTTTC TTGTGATACC TTCTATTGG
2161 AAACTTTGT AGTCTTTACA TTTCTATTGT TTAACATGAA ATCTCAAAAA ATGCCAAATC
2221 AATTCTCAAT TTTAAATTTA GTAGCTCTTG AC
```

*Arabidopsis thaliana* KAS II (NP_849888) Nucleotide sequence

FIG. 4

Weight Percent of Fatty Acids in Exemplary Fats and Oils

| Fatty Acid Fat or Oil | C8:0 | C10:0 | C12:0 | C14:0 | C16:0 | C16:1 | C18:0 | C18:1 | C18:2 | C18:3 | C20:0 C22:0 | C20:1 C22:1 | Other |
|---|---|---|---|---|---|---|---|---|---|---|---|---|---|
| Yellow grease | -- | -- | -- | -- | 23 | 1 | 10 | 50 | 15 | -- | -- | -- | -- |
| Tallow | -- | -- | 0.2 | 2-3 | 25-30 | 2-3 | 21-26 | 39-42 | 2 | -- | 0.4-1 | 0.3 | 0.5 |
| Lard | 1-2 | -- | -- | 1 | 25-30 | 2-5 | 12-16 | 41-51 | 4-22 | -- | -- | 2-3 | 0.2 |
| Butter | 1-2 | 2-3 | 1-4 | 8-13 | 25-32 | 2-5 | 25-33 | 22-29 | 3 | -- | 0.4-2 | 2-3.5 | 1-2 |
| Coconut | 5-9 | 4-10 | 44-51 | 13-18 | 7-10 | -- | 1-4 | 5-8 | 1-3 | -- | 1-2 | -- | 1 |
| Palm Kernel | 2-4 | 3-7 | 45-52 | 14-19 | 6-9 | 0-1 | 1-3 | 10-18 | 1-2 | -- | -- | -- | -- |
| Palm | -- | -- | -- | 1-6 | 32-47 | -- | 1-6 | 40-52 | 2-11 | -- | -- | -- | -- |
| Sunflower | -- | -- | -- | -- | 5.2 | -- | 2.2 | 76.3 | 16.2 | -- | -- | -- | -- |
| Peanut | -- | -- | -- | 0.5 | 6-11 | 1-2 | 3-6 | 39-66 | 17-38 | -- | 5-10 | 2-3 | -- |
| Cottonseed | -- | -- | -- | 0-3 | 17-23 | 1-2 | 1-3 | 23-41 | 34-55 | -- | -- | 0-2 | -- |
| Corn | -- | -- | -- | 0-2 | 8-10 | 1-2 | 1-4 | 30-50 | 34-56 | 0-3 | 1-4 | 0-2 | -- |
| Sunflower | -- | -- | -- | -- | 6.0 | 0.1 | 4.2 | 18.7 | 69.3 | 0.3 | -- | -- | -- |
| Soybean | -- | -- | -- | 0-3 | 7-11 | 0-2 | 3-6 | 22-34 | 50-60 | 2-10 | 5-10 | -- | -- |
| Rapeseed | -- | -- | -- | -- | 2-5 | -- | 1-2 | 10-15 | 10-20 | 5-10 | 1-9 | 50-60 | -- |
| Linseed | -- | -- | -- | 0.2 | 5-9 | -- | 0-1 | 9-29 | 8-29 | 45-67 | -- | -- | -- |
| Tung | -- | -- | -- | -- | -- | -- | -- | 4-15 | 8-15 | 72-88 | -- | -- | -- |

FIG. 6

SEQUENCE LISTING

```
<160> NUMBER OF SEQ ID NOS: 4

<210> SEQ ID NO 1
<211> LENGTH: 356
<212> TYPE: PRT
<213> ORGANISM: Brassica napus
<220> FEATURE:
<221> NAME/KEY: MOD_RES
<222> LOCATION: (53)..(53)
<223> OTHER INFORMATION: Any amino acid
<220> FEATURE:
<221> NAME/KEY: MOD_RES
<222> LOCATION: (106)..(106)
<223> OTHER INFORMATION: Any amino acid
<220> FEATURE:
<221> NAME/KEY: MOD_RES
<222> LOCATION: (129)..(129)
<223> OTHER INFORMATION: Any amino acid
<220> FEATURE:
<221> NAME/KEY: MOD_RES
<222> LOCATION: (136)..(136)
<223> OTHER INFORMATION: Any amino acid
<220> FEATURE:
<221> NAME/KEY: MOD_RES
<222> LOCATION: (185)..(185)
<223> OTHER INFORMATION: Any amino acid

<400> SEQUENCE: 1

Met Val Ala Thr Ser Ala Thr Ser Ser Phe Phe Pro Leu Pro Ser Phe
1               5                   10                  15

Pro Leu Asp Pro Thr Ala Lys Thr Asn Lys Val Thr Thr Ser Thr Asn
            20                  25                  30

Phe Ser Gly Leu Ser Pro Thr Pro Asn Ser Ser Gly Arg Met Lys Val
        35                  40                  45

Lys Pro Asn Ala Xaa Ala Pro Pro Lys Ile Asn Gly Lys Arg Val Gly
```

```
                50                  55                  60
Leu Pro Ser Gly Ser Val Lys Pro Asp Asn Glu Thr Ser Ser Gln His
 65                  70                  75                  80

Pro Ala Ala Pro Arg Thr Phe Ile Asn Gln Leu Pro Asp Trp Ser Met
                 85                  90                  95

Leu Leu Ala Ala Ile Thr Thr Val Phe Xaa Ala Ala Glu Lys Gln Trp
            100                 105                 110

Met Met Leu Asp Trp Lys Pro Arg Arg Ser Asp Val Ile Met Asp Pro
        115                 120                 125

Xaa Gly Leu Gly Arg Ile Val Xaa Asp Gly Leu Val Phe Arg Gln Asn
    130                 135                 140

Phe Ser Ile Arg Ser Tyr Glu Ile Gly Ala Asp Arg Ser Ala Ser Ile
145                 150                 155                 160

Glu Thr Val Met Asn His Leu Gln Glu Thr Ala Leu Asn His Val Lys
                165                 170                 175

Thr Ala Gly Leu Leu Gly Asp Gly Xaa Gly Ser Thr Pro Glu Met Val
            180                 185                 190

Lys Lys Asn Leu Ile Trp Val Val Thr Arg Met Gln Val Val Asp
        195                 200                 205

Lys Tyr Pro Thr Trp Gly Asp Val Val Glu Val Asp Thr Trp Val Ser
210                 215                 220

Gln Ser Gly Lys Asn Gly Met Arg Arg Asp Trp Leu Val Arg Asp Gly
225                 230                 235                 240

Asn Thr Gly Glu Ile Leu Thr Arg Ala Ser Ser Val Trp Val Met Met
                245                 250                 255

Asn Lys Leu Thr Arg Arg Leu Ser Lys Ile Pro Glu Glu Val Arg Gly
            260                 265                 270

Glu Ile Glu Pro Tyr Phe Val Asn Ser Asp Pro Val Leu Ala Glu Asp
        275                 280                 285

Ser Arg Lys Leu Thr Lys Leu Asp Asp Lys Thr Ala Asp Tyr Val Arg
    290                 295                 300

Ser Gly Leu Thr Pro Arg Trp Ser Asp Leu Asp Val Asn Gln His Val
305                 310                 315                 320

Asn Asn Val Lys Tyr Ile Gly Trp Ile Leu Glu Ser Ala Pro Val Gly
                325                 330                 335

Met Met Glu Ser Gln Lys Leu Lys Ser Met Thr Leu Glu Tyr Arg Lys
            340                 345                 350

Glu Cys Gly Arg
        355

<210> SEQ ID NO 2
<211> LENGTH: 412
<212> TYPE: PRT
<213> ORGANISM: Arabidopsis thaliana

<400> SEQUENCE: 2

Met Val Ala Thr Ser Ala Thr Ser Ser Phe Phe Pro Val Pro Ser Ser
 1               5                  10                  15

Ser Leu Asp Pro Asn Gly Lys Gly Asn Lys Ile Gly Ser Thr Asn Leu
                20                  25                  30

Ala Gly Leu Asn Ser Ala Pro Asn Ser Gly Arg Met Lys Val Lys Pro
            35                  40                  45

Asn Ala Gln Ala Pro Pro Lys Ile Asn Gly Lys Lys Val Gly Leu Pro
    50                  55                  60

Gly Ser Val Asp Ile Val Arg Thr Asp Thr Glu Thr Ser Ser His Pro
```

```
             65                  70                  75                  80
Ala Pro Arg Thr Phe Ile Asn Gln Leu Pro Asp Trp Ser Met Leu Leu
                    85                  90                  95

Ala Ala Ile Thr Thr Ile Phe Leu Ala Ala Glu Lys Gln Trp Met Met
                    100                 105                 110

Leu Asp Trp Lys Pro Arg Arg Ser Asp Met Leu Val Asp Pro Phe Gly
            115                 120                 125

Ile Gly Arg Ile Val Gln Asp Gly Leu Val Phe Arg Gln Asn Phe Ser
        130                 135                 140

Ile Arg Ser Tyr Glu Ile Gly Ala Asp Arg Ser Ala Ser Ile Glu Thr
145                 150                 155                 160

Val Met Asn His Leu Gln Glu Thr Ala Leu Asn His Val Lys Thr Ala
                    165                 170                 175

Gly Leu Leu Gly Asp Gly Phe Gly Ser Thr Pro Glu Met Phe Lys Lys
                    180                 185                 190

Asn Leu Ile Trp Val Val Thr Arg Met Gln Val Val Asp Lys Tyr
            195                 200                 205

Pro Thr Trp Gly Asp Val Glu Val Asp Thr Trp Val Ser Gln Ser
        210                 215                 220

Gly Lys Asn Gly Met Arg Arg Asp Trp Leu Val Arg Asp Cys Asn Thr
225                 230                 235                 240

Gly Glu Thr Leu Thr Arg Ala Ser Ser Val Trp Val Met Met Asn Lys
                    245                 250                 255

Leu Thr Arg Arg Leu Ser Lys Ile Pro Glu Glu Val Arg Gly Glu Ile
                    260                 265                 270

Glu Pro Tyr Phe Val Asn Ser Asp Pro Val Leu Ala Glu Asp Ser Arg
            275                 280                 285

Lys Leu Thr Lys Ile Asp Asp Lys Thr Ala Asp Tyr Val Arg Ser Gly
        290                 295                 300

Leu Thr Pro Arg Trp Ser Asp Leu Asp Val Asn Gln His Val Asn Asn
305                 310                 315                 320

Val Lys Tyr Ile Gly Trp Ile Leu Glu Ser Ala Pro Val Gly Ile Met
                    325                 330                 335

Glu Arg Gln Lys Leu Lys Ser Met Thr Leu Glu Tyr Arg Arg Glu Cys
                    340                 345                 350

Gly Arg Asp Ser Val Leu Gln Ser Leu Thr Ala Val Thr Gly Cys Asp
            355                 360                 365

Ile Gly Asn Leu Ala Thr Ala Gly Asp Val Glu Cys Gln His Leu Leu
        370                 375                 380

Arg Leu Gln Asp Gly Ala Glu Val Val Arg Gly Arg Thr Glu Trp Ser
385                 390                 395                 400

Ser Lys Thr Pro Thr Thr Thr Trp Gly Thr Ala Pro
                    405                 410

<210> SEQ ID NO 3
<211> LENGTH: 541
<212> TYPE: PRT
<213> ORGANISM: Arabidopsis thaliana

<400> SEQUENCE: 3

Met Val Gly Ala Ser Ser Ser Tyr Ala Ser Pro Leu Cys Thr Trp Phe
1               5                   10                  15

Val Ala Ala Cys Met Ser Val Ser His Gly Gly Asp Ser Arg Gln
            20                  25                  30

Ala Val Ala Leu Gln Ser Gly Gly Arg Ser Arg Arg Arg Arg Gln Leu
```

-continued

```
                35                  40                  45
Ser Lys Cys Ser Val Ala Ser Gly Ser Ala Ser Ile Gln Ala Leu Val
 50                  55                  60

Thr Ser Cys Leu Asp Phe Gly Pro Cys Thr His Tyr Asn Asn Asn Asn
 65                  70                  75                  80

Ala Leu Ser Ser Leu Phe Gly Ser Asn Ser Val Ser Leu Asn Arg Asn
                 85                  90                  95

Gln Arg Arg Leu Asn Arg Ala Ala Ser Ser Gly Gly Ala Met Ala Val
                100                 105                 110

Met Glu Met Glu Lys Glu Ala Ala Val Asn Lys Lys Pro Pro Thr Glu
                115                 120                 125

Gln Arg Arg Val Val Val Thr Gly Met Gly Val Glu Thr Ser Leu Gly
                130                 135                 140

His Asp Pro His Thr Phe Tyr Glu Asn Leu Leu Gln Gly Asn Ser Gly
145                 150                 155                 160

Ile Ser Gln Ile Glu Asn Phe Asp Cys Ser Glu Phe Pro Thr Arg Ile
                165                 170                 175

Ala Gly Glu Ile Lys Ser Phe Ser Thr Glu Gly Trp Val Ala Pro Lys
                180                 185                 190

Leu Ser Lys Arg Met Asp Lys Phe Met Leu Tyr Leu Leu Thr Ala Gly
                195                 200                 205

Lys Lys Ala Leu Ala Asp Gly Gly Val Thr Asp Glu Val Met Ala Glu
210                 215                 220

Phe Asp Lys Thr Lys Cys Gly Val Leu Ile Gly Ser Ala Met Gly Gly
225                 230                 235                 240

Met Lys Val Phe Tyr Asp Ala Ile Glu Ala Leu Arg Ile Ser Tyr Lys
                245                 250                 255

Lys Met Asn Pro Phe Cys Val Pro Phe Ala Thr Thr Asn Met Gly Ser
                260                 265                 270

Ala Met Leu Ala Met Asp Leu Gly Trp Met Gly Pro Asn Tyr Ser Ile
                275                 280                 285

Ser Thr Ala Cys Ala Thr Ser Asn Phe Cys Ile Leu Asn Ser Ala Asn
290                 295                 300

His Ile Ile Lys Gly Glu Ala Asp Val Met Leu Cys Gly Gly Ser Asp
305                 310                 315                 320

Ala Val Ile Ile Pro Ile Gly Leu Gly Gly Phe Val Ala Cys Arg Ala
                325                 330                 335

Leu Ser Gln Arg Asn Asn Asp Pro Thr Lys Ala Ser Arg Pro Trp Asp
                340                 345                 350

Thr Asn Arg Asp Gly Phe Val Met Gly Glu Gly Ala Gly Val Leu Leu
                355                 360                 365

Leu Glu Glu Leu Glu His Ala Lys Lys Arg Gly Ala Thr Ile Tyr Ala
370                 375                 380

Glu Phe Leu Gly Gly Ser Phe Thr Cys Asp Ala Tyr His Met Thr Glu
385                 390                 395                 400

Pro His Pro Asp Gly Ala Gly Val Ile Leu Cys Ile Glu Arg Ala Leu
                405                 410                 415

Ala Ser Ala Gly Ile Ser Lys Glu Gln Ile Asn Tyr Ile Asn Ala His
                420                 425                 430

Ala Thr Ser Thr His Ala Gly Asp Ile Lys Glu Tyr Gln Ala Leu Ala
                435                 440                 445

His Cys Phe Gly Gln Asn Pro Glu Leu Lys Val Asn Ser Thr Lys Ser
450                 455                 460
```

```
Met Ile Gly His Leu Leu Gly Ala Ala Gly Ala Val Glu Ala Val Ala
465                 470                 475                 480

Thr Val Gln Ala Ile Arg Thr Gly Trp Val His Pro Asn Ile Asn Leu
                485                 490                 495

Glu Asn Pro Asp Ser Gly Val Asp Thr Lys Leu Leu Val Gly Pro Lys
            500                 505                 510

Lys Glu Arg Leu Asp Ile Lys Ala Ala Leu Ser Asn Ser Phe Gly Phe
        515                 520                 525

Gly Gly His Asn Ser Ser Ile Ile Phe Ala Pro Tyr Lys
    530                 535                 540

<210> SEQ ID NO 4
<211> LENGTH: 2252
<212> TYPE: DNA
<213> ORGANISM: Arabidopsis thaliana

<400> SEQUENCE: 4
atttgtatag tgttgtatct ctctctctct ctctctgtct gtttgtttca gagaaggatt    60
tttggcgtct ccacgcacga tttaacgcat cgaagctctc tgcacgcttc ctgaaagaga   120
gagagaagag agagatcgca gatcgatttc tcttaaatct ctcgtgaatc ccatttgcct   180
tctctctgct agattctctc ttcttctctt cacccatttc tcgctttctc ctttgttctc   240
tcatctgggt tcttctcaaa gcctcttcct ttttatgcca tggtgggtgc gtcttcctct   300
tacgcatctc cgttatgtac ctggtttgtt gctgcttgca tgtccgtctc tcacggtgga   360
ggagatagcc gtcaggctgt tgctcttcaa tctggtgggc ggagtcggcg aaggaggcag   420
cttagcaaat gctctgtcgc ttctggatcc gctagcattc aggctctcgt cacttcttgt   480
ttggattttg gtccttgtac tcactacaac aacaacaatg cattgtcttc tctctttgga   540
tcgaatagtg tttctttgaa tcgaaaccag aggagattga atcgtgctgc tagctccggt   600
ggagccatgg cagtgatgga gatggaaaag gaagctgcgg ttaacaagaa accacctacg   660
gagcagcgtc gagttgtagt gacaggcatg ggagttgaaa catcattggg tcatgaccca   720
cataccttct atgagaattt gctacaaggc aacagtggta ttagccagat tgaaaatttt   780
gattgttctg aatttcctac gcgaattgcg ggagagatca aaagcttctc gactgaagga   840
tgggttgctc caaaactttc taaaggatg acaaattca tgctctatct tctcacagct   900
ggtaagaaag ctttggctga tggtggggtt actgatgaag taatggcaga gtttgacaaa   960
accaaatgtg gagttttgat tggctcggca atgggaggaa tgaaggtctt ttacgatgct  1020
attgaagctc tgagaatctc ttacaagaag atgaatcctt tttgtgtacc ttttgcgaca  1080
acaaacatgg ttctgctat gcttgccatg gatctgggat ggatgggcc aaactattct  1140 atttcaactg cttgtgccac aagcaacttt tgcattctga attcagcaaa ccacattatt  1200
aaaggtgaag ctgatgtaat gctctgtggt ggctcagatg cagttattat tccaataggg  1260
ttgggaggtt ttgttgcatg ccgggctctt tcacaaagga ataatgatcc cacaaaagct  1320
tcacgtcctt gggataccaa tcgagatggt ttcgtgatgg agagggagc tggagttcta  1380 cttttggaag aactcgagca tgctaagaaa agaggtgcaa ctatctacgc agagttcctc  1440
ggtgggagtt tcacatgtga tgcctatcac atgaccgagc ctcaccctga tggggctggt  1500
gttattctct gtattgagag agcgttagct agtgctggga tttccaagga caaataaat  1560 tacataaatg cacatgcaac ctcaacgcat gctggagata ttaaggaata ccaagccctt  1620
gctcactgtt ttgccaaaaa tcctgagctt aaggtaaatt ccacaaaatc tatgattgga  1680
cacttgctgg gagctgctgg ggccgtggag ctgttgcaa ctgtgcaggc gatacggacc  1740
```

```
ggatgggttc atccaaatat caacctcgag aatccagaca gtggagtgga tacaaagctg    1800
ctggtgggtc ctaagaagga gagactggac attaaagcag ccttgtcaaa ttcattcggg    1860
tttggtggtc ataactccag catcattttt gctccttaca agtgaaagcg aaagcagttg    1920
cttgtactcc aaacctgatt gtataacttg ctgtaagtgt tttacaagaa gtttcccatg    1980
ttatgctagt gttacgtcga gggaatcaac agagtttgtt caactaccaa gagctaagct    2040
aagtttctta ggatcaagat ctgatgagcc aaagacttgg acaggagcta aaacgtgcta    2100
gagatatcag agtttggatt cgccattaaa attctgtttc ttgtgatacc ttcttattgg    2160
aaatctttgt agtctttaca tttctattgt ttaacatgaa atctcaaaaa atgccaaatc    2220
aattctcaat tttaaattta gtagctcttg ac                                  2252
```

FATTY ACID BLENDS AND USES THEREFOR

CROSS-REFERENCE TO RELATED APPLICATIONS

The present application is a divisional application of U.S. patent application Ser. No. 12/306,477, filed Nov. 4, 2009, which is a US National Stage Entry Application of PCT Application No. PCT/US2007/015017, filed Jun. 27, 2007, which claims priority to U.S. Provisional Patent Application No. 60/817,558, filed Jun. 28, 2006, all of which are titled Fatty Acid Blends and Uses Therefor, each of which are incorporated herein by reference in their entirety, including figures.

SEQUENCE LISTING

The instant application contains a Sequence Listing which has been submitted in ASCII format via EFS-Web and is hereby incorporated by reference in its entirety. Said ASCII copy, created on Nov. 17, 2011, is named 74267202.txt and is 15,139 bytes in size.

FIELD OF THE INVENTION

Provided are oils; blends of oils or fatty acids; uses of such blends, including uses as fuels; and methods of obtaining oils or fatty acids blends.

BACKGROUND OF THE INVENTION

The following description of the background of the invention is provided simply as an aid in understanding the invention and is not admitted to describe or constitute prior art to the invention.

Vegetable oils have been used as alternative fuels and feedstocks for the production of biodiesels. Generally the oils used are extracted from plants grown in large quantity in a particular region. Therefore, soybean oil is of interest as a source of biodiesel in the United States, whereas rapeseed oil is of interest in European countries; and countries having tropical climates utilize coconut oil or palm oil (Knothe et al., published on-line at the URL www.biodiesel.org/resources/reportsdatabase/reports/gen/19961201_gen-162.pdf).

A composition of triglycerides simulating the oil from VS-320, a mutant *Cuphea viscossima*, is disclosed by Geller et al. (*Transactions of the American Society of Agricultural Engineers* 42:859-862, 1999). The "simulated analogue of VS-320 oil" disclosed in Geller has a triglyceride composition of 4.2% C6:0; 40.20% C8:0; 36.90% C10:0; 4.80% C12:0; 6.80% C14:0; 3.33% C16:0; 0.00% C18:0; 1.37% C18:1; 2.05% C18:2; and 0.00% C18:3 (see Table 1). Geller et al., (1999) concluded that "[t]his model suggests that an increase in the C8:0 content of vegetable oils along with a subsequent reduction in medium- and long-chain triglycerides may result in a more efficient, better performing alternative diesel fuel."

Stournas, et al., (*JACOS*, 1995, 72:433-437) discloses characteristics of various oils as fuels and states "[g]iven the ±3° C. repeatability of pour point determinations, most of the added components did not appear to affect the −12° C. pour point of the base fuel to a significant degree. The major exceptions are the saturated fatty alcohols with $C_{12}$ and longer alkyl chains, which increase the pour point substantially; minor negative effects were also observed with some of the longer-chain esters. It is worth noticing that the presence of the double bond in all oleate derivatives sharply improves their cold flow behavior in comparison to the corresponding stearates" and "[w]hen both ignition quality and cold flow behavior are taken into account, the tertiary dimethylamines are the best performers; however, the tertiary amides also appear to be interesting prospects, in that their preparation from the glycerides of natural vegetable oils may be much simpler than that of the amines, as some recent studies have shown."

Mittelbach (*Bioresource Technology*, 1996, 56:7-11) discusses specifications and quality control of diesel fuel derived from vegetable oils and states "[o]ne parameter which has not yet been included in the Austrian standards for RME, but might be necessary when defining general standards for fatty acid methyl esters is the iodine number, which describes the content of unsaturated fatty acids and is only dependent on the origin of the vegetable oil. In Germany a value of 115 is defined, which corresponds to rapeseed oil, but would exclude different kinds of oils, like sunflower oil and soybean oil. A limitation of unsaturated fatty acids may be necessary, due to the fact that heating higher unsaturated fatty acids results in polymerization of glycerides. This can lead to the formulation of deposits or to deterioration of the lubricating oil. This effect increases with the number of double bonds in the fatty acid chain. Therefore, it seems better to limit the content of higher unsaturated fatty acids like linolenic acid, than to limit the degree of unsaturation with the iodine number."

Graboski (*Prog. Energy Combustion Sci.*, 1998, 24:125-164) discusses "the statues of fat and oil derived diesel fuels with respect to fuel properties, engine performance, and emissions" and states "[r]educing chain length and/or increasing chain branching would improve the cold flow properties of the fuel. Chain length and degree of branching might be altered through both plant breeding or genetic engineering approaches, as well as through chemical processing of the biodiesel to cleave certain double bonds or to form branched isomers. Very little practical research has been done in the chemical processing area. The cold flow properties of biodiesel fuels are clearly an area in need of considerable research."

Goodrum et al., (*Bioresource Technology*, 1996, 56:55-60) discusses "physical properties of low molecular weight triglycerides for the development of bio-diesel fuel models" and states "[o]ils which contain significant fractions of low molecular weight triglycerides might be suitable for direct use as fuel extenders. In fact, feedstock from *Cuphea* species (Graham, 1989), contains oils predominantly composed of these triglycerides (particularly tricaprylin and tricaprin). Modern DNA transfer technologies might also afford the transfer of genes that control the synthesis of low molecular weight triglycerides from species such as *Cuphea* into other more well-established oilseed crops. Oil composition could then be genetically modified for the optimal desired biodiesel properties."

Knothe (*Fuel Processing Technology*, 2005, 86:1059-1070) states "[s]aturated fatty compounds have significantly higher melting points than unsaturated fatty compounds (Table 1) and in a mixture they crystallize at higher temperature than the unsaturates. Thus biodiesel fuels derived from fats or oils with significant amounts of saturated fatty compounds will display higher cloud points and pour points."

Kinney et al., (*Fuel Processing Technology*, 2005, 86:1137-1147) discusses issues regarding modification of soybean oil for enhanced performance biodiesel blends. This article references the blends disclosed in Geller et al., 1999 and states "since the melting point of biodiesel derived from these short-chain fatty acids is fairly high, additional winterization steps would be required to improve cold flow properties." Kinney et al. also states "[a]lterations in the fatty acid profile that increase the saturated fatty acid content will augment oxidative stability but worsen cold flow . . . the presence of double bonds in fatty acids will lower the cetane number; hence, strategies to shift the fatty pool of a vegetable oil towards saturated moieties will improve ignition quality of the derived biodiesel, but as with oxidative stability may compromise cold flow properties."

U.S. Pat. No. 4,364,743 ("the '743 patent") discloses "a synthetic fuel of fatty acid esters [that] provides a novel source of energy when burned alone or in combination with other known fuels," and that "[e]sters are preferably prepared by a transesterification reaction using various oils such as soya oil, palm oil, safflower oil, peanut oil, corn oil, cottonseed oil, linseed oil, oiticica oil, tung oil, coconut oil, castor oil, perilla oil, rapeseed oil, sunflower oil, lard, tallow, fish oils, blubber, lipids from marine and land animals and lipids from vegetable sources."

U.S. Pat. No. 5,389,113 ("the '113 patent") discloses "mixtures containing a) 58 to 95% by weight of at least one ester with an iodine value of 50 to 150 derived from fatty acids containing 12 to 22 carbon atoms and lower aliphatic alcohols containing 1 to 4 carbon atoms, b) 4 to 40% by weight of at least one ester of fatty acids containing 6 to 14 carbon atoms and lower aliphatic alcohols containing 1 to 4 carbon atoms and c) 0.1 to 2% by weight of at least one polymeric ester."

US Patent Application Publication No. 2006026963 discloses "nucleic acid constructs and methods for producing altered seed oil compositions" and states "a method to enhance oleic acid content and reduce saturated fatty acid content in a plant seed comprising i) shortening the length of a first heterologous FAD2 sequence until the amount of FAD2 gene suppression from a plant transformed with the first heterologous FAD2 sequence is at least partially reduced relative to the amount of FAD2 gene suppression in a plant cell comprising a similar genetic background and a second heterologous FAD2 sequence, wherein the second heterologous FAD2 sequence consists of more endogenous FAD2 sequence than the first heterologous FAD2 sequence; ii) expressing a heterologous FATB sequence capable of at least partially reducing FATB gene expression in a plant cell relative to the suppression of FATB in a plant cell with a similar genetic background but without the heterologous FATB sequence; iii) growing a plant comprising a genome with the first heterologous FAD2 sequence and the heterologous FATB sequence; and iv) cultivating a plant that produces seed with a reduced saturated fatty acid content relative to seed from a plant having a similar genetic background but lacking the first heterologous FAD2 sequence and the heterologous FATB sequence."

SUMMARY OF THE INVENTION

Applicant has determined that blends of vegetable oils can be chosen so that the blend exhibits desirable properties for use as alternative fuels or as feedstocks for the production of a biodiesel. For example, such blends may be chosen so that, when used as a fuel in a cold climate, the blend is less likely to freeze. Blends may also be chosen so that the blend is stable at higher temperatures. Further, blends may be chosen to achieve desirable ignition properties when used as a fuel in a vehicle. Some particular examples of features of the blends of oils or fatty acids of the invention are described below. It is understood that the blends of oils or fatty acids within the invention may have any combination of the features described in the below embodiments. In particular the Inventors have determined that certain mixtures of fatty acids have surprisingly beneficial properties for production of biofuels. For example, the Inventors have found that particular balances of medium chain fatty acids and monounsaturated fatty acids can have surprisingly beneficial properties, for example with respect to cold weather capabilities. In certain embodiments of the fatty acid mixtures having balanced amounts of medium chain fatty acids (for example C8, C10 and C12) and monounsaturated fatty acids (preferably C16:1 and C18:1), Inventors have found that the presence C16:0 and C18:0 can have particularly unfavorable effects on cold flow properties and therefore reduced levels of C16:0 and C18:0 in a biodiesel can be beneficial for cold weather capabilities; and that C14:0, C18:2, C18:3, C20, C22 and C24 can also adversely effect cold flow properties; thus, reducing these fatty acids in a biodiesel can also be beneficial.

The term "oil" as used herein, refers to a substance composed primarily of triglycerides of fatty acids. Vegetable oils may be extracted from various parts of the plant, including the seeds, fruit, or leaves of plants. It is generally liquid at room temperatures. In some embodiments the oils are derived from canola, rapeseed, palm, palm kernel, coconut, tucum, sunflower, safflower, olive, *macadamia*, babassu, castor, peanut, cotton, flaxseed, linseed, cohune, and jatropha. In further embodiments, the oils may be derived from a genetically modified plant.

Triglycerides are the main constituents of vegetable oils and animal fats. Triglycerides may be solid or liquid at room temperature. A triglyceride, also called triacylglycerol (TAG), is a chemical compound formed from one molecule of glycerol and three fatty acids. Glycerol is a trihydric alcohol (containing three hydroxyl groups) that can combine with up to three fatty acids to form monoglycerides, diglycerides, and triglycerides, when combined with one, two or three fatty acids, respectively. Monoglycerides, diglycerides, and triglycerides are classified as esters, which are compounds created by the reaction between acids and alcohols that release water as a by-product. Fatty acids may combine with any of the three hydroxyl groups to form and ester linkage and create a wide diversity of compounds. Further, fatty acids having different lengths may combine with an individual glycerol molecule. Thus the resulting diglyceride or triglyceride may comprise different fatty acids within the same triglyceride molecule.

Fatty acids are composed of carbon, hydrogen, and oxygen arranged as a carbon chain skeleton with a carboxyl group at one end. Fatty acids may be saturated fatty acids (SFAs) and have no carbon-carbon double bonds, monounsaturated (MUFAs) and have one carbon-carbon double bond, or polyunsaturated fatty acids (PUFAs) and have more than one carbon-carbon double bond. The number of carbons in a fatty acid chain and the number of carbon-carbon double bonds is commonly expressed as "number of carbons:number of carbon-carbon double bonds." For example, oleic acid, which has 18 carbons and one double bond, can be expressed as "C18:1" or "18:1."

"Medium chain fatty acids" as used herein refers to fatty acids containing 6 to 14 carbons, preferably 8 to 12 carbons.

"Long chain fatty acids" as used herein refers to fatty acids containing more than 14 carbons, or more that 16 carbons, or even more than 18 carbons.

In one aspect, mixtures of fatty acids are provided.

In certain preferred embodiments of the mixtures of fatty acids provided herein, lauric acid accounts for 6% to 20% of the mixture; more preferably 6% to 10% of the mixture.

In certain preferred embodiments of the mixtures of fatty acids provided herein, caprylic acid (C8:0), capric acid (C10: 0), and lauric acid (C12:0) together account for between 20% and 40% of the mixture; or between 20% and 30% of the mixture; or between 30% and 40% of the mixture; or between 25% and 35% of the mixture. In other of embodiments of the mixtures of fatty acids provided herein, caprylic acid (C8:0), capric acid (C10:0), and lauric acid (C12:0) together account for between 60% and 85% of the mixture; or between 60% and 70% of the mixture; or between 70% and 85% of the mixture; or between 65% and 75% of the mixture. In yet other of embodiments of the mixtures of fatty acids provided herein, caprylic acid (C8:0), capric acid (C10:0), and lauric acid (C12:0) together account for between 40% and 60% of the mixture; or between 40% and 50% of the mixture; or between 50% and 60% of the mixture; or between 45% and 55% of the mixture.

In some preferred embodiments of the mixtures of fatty acids provided herein, monounsaturated fatty acids account for between 5% to 95% of the mixture; preferably monounsaturated fatty acids account for more than 10%, or more than 15%; or more than 20%; or more than 25%; or more than 30%; or more than 35%; or more than 40%; or more than 45; or more than 50%; or more than 60%; or more than 65%; or more than 70%; or more than 80%; or more than 85% of the mixture.

In certain preferred embodiments of the mixtures of fatty acids provided herein, oleic acid (C18:1) and palmitoleic acid (16:1) together account for between 20% and 85% of the mixture; or between 20% and 40% of the mixture; or between 20% and 30% of the mixture; or between 30% and 40% of the mixture; or between 25% and 35% of the mixture; or between 40% and 60% of the mixture; or between 35% and 55% of the mixture; or between 55% and 65% of the mixture; or between 60% and 85% of the mixture; or between 60% and 70% of the mixture; or between 70% and 85% of the mixture; or between 65% and 75% of the mixture.

In some preferred embodiments of the mixtures of fatty acids provided herein, caprylic acid (C8:0), capric acid (C10:0), lauric acid (C12:0), oleic acid (C18:1) and palmitoleic acid (16:1) together account for more than 50% of the mixture; or more than 55% of the mixture; or more than 60% of the mixture; or more than 65% of the mixture; or more than 70% of the mixture; or more than 75% of the mixture; or more than 80% of the mixture; or more than 85% of the mixture; or more than 90% of the mixture.

In some preferred embodiments of the mixtures of fatty acids provided herein, stearic (18:0) and palmitic acid (16:0) together account for less than 25% of the mixture; more preferably less than 15% of the mixture; more preferably less than 10% of the mixture; more preferably less than 8% of the mixture; more preferably less than 6% of the mixture; more preferably less than 5% of the mixture; more preferably less than 4% of the mixture; more preferably less than 3% of the mixture; more preferably less than 2% of the mixture; or less than 1% of the mixture; or less than 0.5% of the mixture; or in some preferred embodiments the mixture of fatty acids are substantially free of stearic (18:0) and palmitic acid (16:0).

In some preferred embodiments of the mixtures of fatty acids provided herein, myristic acid (14:0) accounts for less than 25% of the mixture; more preferably less than 15% of the mixture; more preferably less than 10% of the mixture; more preferably less than 8% of the mixture; more preferably less than 6% of the mixture; more preferably less than 5% of the mixture; more preferably less than 4% of the mixture; more preferably less than 3% of the mixture; more preferably less than 2% of the mixture; or less than 1% of the mixture; or less than 0.5% of the mixture; or in some preferred embodiments the mixture of fatty acids are substantially free of myristic acid (14:0).

In some preferred embodiments of the mixtures of fatty acids provided herein, linoleic acid (18:2) and linolenic acid (18:3) together account for less than 25% of the mixture; more preferably less than 15% of the mixture; more preferably less than 10% of the mixture; more preferably less than 8% of the mixture; more preferably less than 6% of the mixture; more preferably less than 5% of the mixture; more preferably less than 4% of the mixture; more preferably less than 3% of the mixture; more preferably less than 2% of the mixture; or less than 1% of the mixture; or less than 0.5% of the mixture; or in some preferred embodiments the mixture of fatty acids are substantially free of linoleic acid (18:2) and linolenic acid (18:3).

In some preferred embodiments of the mixtures of fatty acids provided herein, arachidic acid (C20:0), behenic acid (C22:0) and lignoceric acid (C24:0) together account for less than 25% of the mixture; more preferably less than 15% of the mixture; more preferably less than 10% of the mixture; more preferably less than 8% of the mixture; more preferably less than 6% of the mixture; more preferably less than 5% of the mixture; more preferably less than 4% of the mixture; more preferably less than 3% of the mixture; more preferably less than 2% of the mixture; or less than 1% of the mixture; or less than 0.5% of the mixture; or in some preferred embodiments the mixture of fatty acids are substantially free of arachidic acid (C20:0), behenic acid (C22:0) and lignoceric acid (C24:0).

In certain aspects, a mixture of fatty acids is provided wherein saturated fatty acids having 8-12 carbons and monounsaturated fatty acids having 12-18 carbons account for between 80% and 100% of the mixture, caprylic acid (C8:0) and capric acid (C10:0) account for between 5% and 80% of the mixture, lauric acid accounts for less than 20% of the mixture, and polyunsaturated fatty acids and saturated fatty acids having more than 12 carbons together account for less than 20% of the mixture. In certain preferred embodiments of the aforementioned mixture of fatty acids caprylic acid (C8:0), capric acid (C10:0), and lauric acid (C12:0) together account for 20% to 40% of the mixture; preferably lauric acid (C12:0) comprises 6% to 20% of the mixture, more preferably lauric acid (C12:0) comprises 6% to 10% of the mixture. In some preferred embodiments of the mixture, oleic acid (C18:1) and palmitoleic acid (16:1) together account for 50% to 85% of the mixture.

In certain aspects, a mixture of fatty acids is provided wherein saturated fatty acids having 8-12 carbons and monounsaturated fatty acids having 12-18 carbons account for between 80% and 100% of the mixture, caprylic acid (C8:0) and capric acid (C10:0) account for between 5% and 80% of the mixture, lauric acid accounts for less than 20% of the mixture, and polyunsaturated fatty acids and saturated fatty acids having more than 12 carbons together account for less than 20% of the mixture. In certain preferred embodiments of the aforementioned mixture of fatty acids caprylic acid (C8:0), capric acid (C10:0), and lauric acid (C12:0) together account for 20% to 40% of the mixture; preferably lauric acid (C12:0) comprises 6% to 20% of the mixture, more preferably lauric acid (C12:0) comprises 6 to 10% of the mixture; and oleic acid (C18:1) and palmitoleic acid (16:1) together account for 50% to 85% of the mixture. In other preferred embodiments of the aforementioned mixture, caprylic acid (C8:0), capric acid (C10:0), and lauric acid (C12:0) together account for 60% to 85% of the mixture; preferably lauric acid (C12:0) comprises 6% to 20% of the mixture, more preferably lauric acid (C12:0) comprises 6 to 10% of the mixture; and oleic acid (C18:1) and palmitoleic acid (16:1) together account for 20% to 40% of the mixture.

In one aspect, the invention features blends of two or more oils, wherein at least 50% by weight of the fatty acids are medium chain fatty acids, and wherein caprylic acid (C8:0) comprises up to 25% of the final blend and less than 20% are long chain fatty acids.

In a related aspect, the invention features blends of fatty acids, wherein at least 50% by weight of the fatty acids are medium chain fatty acids, and wherein caprylic acid (C8:0) comprises up to 25% of the final blend and less than 20% are long chain fatty acids.

In some embodiments of the blends of oils or fatty acids of the invention, the blends comprise at least 60% medium chain fatty acids, preferably at least 65% medium chain fatty acids, preferably at least 70% medium chain fatty acids, preferably at least 75% medium chain fatty acids, preferably at least 80% medium chain fatty acids, preferably at least 85% medium chain fatty acids, preferably at least 90% medium chain fatty acids, or preferably at least 95% medium chain fatty acids.

In particular embodiments of the blends of oils or fatty acids of the invention, the blends comprise 5-25% caprylic acid (C8:0); 10-25% caprylic acid (C8:0); 10-20% caprylic acid (C8:0); or 15-25% caprylic acid (C8:0).

In particular embodiments of the blends of oils or fatty acids of the invention, the blends comprise 30-60% capric acid (C10:0); 25-55% capric acid (C10:0); 30-50% capric acid (C10:0); or 40-50% capric acid (C10:0).

In particular embodiments of the blends of oils or fatty acids of the invention, the blends comprise 5-35% lauric acid (C12:0); 10-20% lauric acid (C12:0); 15-25% lauric acid (C12:0); 20-30% lauric acid (C12:0); or 25-35% lauric acid (C12:0).

In other embodiments of the blends of oils or fatty acids of the invention, the blends comprise less than 15% long chain fatty acids, preferably less than 10% long chain fatty acids, preferably less than 7% long chain fatty acids, preferably less than 5% long chain fatty acids, or preferably less than 3% long chain fatty acids.

In still other embodiments of the blends of oils or fatty acids of the invention, the blends comprise less than 15% monounsaturated fatty acids, preferably less than 10% monounsaturated fatty acids, preferably less than 7% monounsaturated fatty acids, preferably less than 5% monounsaturated fatty acids, or preferably less than 2% monounsaturated fatty acids.

In yet other embodiments of the blends of oils or fatty acids of the invention, the blends include less than 10% polyunsaturated fatty acids, preferably less than 7% polyunsaturated fatty acids, preferably less than 5% polyunsaturated fatty acids, preferably less than 3% polyunsaturated fatty acids, or preferably less than 1% polyunsaturated fatty acids.

In particular embodiments of the blends of oils or fatty acids of the invention, the caproic acid (6:0) may be 0 to about 5% by weight of the blend; caprylic acid (8:0) may be about 5 to about 25% by weight of the blend; capric acid (10:0) may be about 30 to about 60% by weight of the blend; lauric acid (12:0) may be about 5 to about 30% by weight of the blend; myristic acid (14:0) may be 0 to about 5% by weight of the blend; palmitic acid (16:0) may be 0 to about 5% by weight of the blend; palmitoleic acid (16:1) may be 0 to about 10% by weight of the blend; stearic acid (18:0) may be 0 to about 5% by weight of the blend; oleic acid (18:1) may be 0 to about 10% by weight of the blend; linoleic acid (18:2) may be 0 to about 5% by weight of the blend; linolenic acid (18:3) may be 0 to about 1% by weight of the blend; arachidic acid (20:0) may be 0 to about 3% by weight of the blend; behenic acid (22:0) may be 0 to about 3% by weight of the blend; erucic acid (22:1) may be 0 to about 5% by weight of the blend; and lignoceric acid (24:0) may be 0 to about 3% by weight of the blend.

In some embodiments of the blends of oils or fatty acids of the invention, the triglycerides of the oils or the fatty acids are converted to fatty acid alkyl esters. In particular embodiments the alkyl esters are methyl esters, ethyl esters, propyl esters, isopropyl esters, or butyl esters. In preferred embodiments, the alkyl esters are methyl esters.

In certain embodiments of invention blends of oils, the oils are derived from vegetable oils or animal fats. In preferred embodiments the oil is selected from the group consisting of canola, rapeseed, palm oil, palm kernel, coconut, tucum, sunflower, safflower, *Cuphea*, olive, *macadamia*, babassu, castor, peanut, cotton, flaxseed, linseed, cohune, and jatropha. In some embodiments of invention blends of oils, the oils are derived from a genetically modified plant. In particular embodiments, the oil is derived from a genetically modified plant wherein the plant has been modified to produce and increased amount of medium chain fatty acids as compared to the native plant. In further embodiments, one or more oils from a native plant or plants may be blended with one or more oils obtained from genetically modified plants.

In some embodiments of the blends of oils or fatty acids of the invention, the oil blend or fatty acid blend is useful as a fuel for powering an internal combustion engine. In other embodiments the oil blend or fatty acid blend is used as a feedstock in the preparation of a fuel additive, a functional fluid, freezing point depressant, a biodiesel, an aviation fuel, a home heating oil, or a substitute for kerosene.

In a related aspect, the invention features blends of fatty acid alkyl esters, wherein at least 50% of the fatty acid alkyl esters are medium chain fatty acid alkyl esters and less than 20% are long chain fatty acid alkyl esters.

In particular embodiments of the invention blends of fatty acid alkyl esters, such blends include at least 60% of medium chain fatty acid alkyl esters, preferably at least 65% medium chain fatty acid alkyl esters, preferably at least 70% medium chain fatty acid alkyl esters, preferably at least 75% medium chain fatty acid alkyl esters, preferably at least 80% medium chain fatty acid alkyl esters, preferably at least 85% medium chain fatty acid alkyl esters, preferably at least 90% medium chain fatty acid alkyl esters, or preferably at least 95% medium chain fatty acid alkyl esters.

In other embodiments of the invention blends of fatty acid alkyl esters, the blends include less than 15% long chain fatty acid alkyl esters, preferably less than 10% long chain fatty acid alkyl esters, preferably less than 7% long chain fatty acid alkyl esters, preferably less than 5% long chain fatty acid alkyl esters, or preferably less than 3% long chain fatty acid alkyl esters.

In still other embodiments of the invention blends of fatty acid alkyl esters, the blends include less than 15% monounsaturated fatty acid alkyl esters, preferably less than 10% monounsaturated fatty acid alkyl esters, preferably less than 7% monounsaturated fatty acid alkyl esters, preferably less than 5% monounsaturated fatty acid alkyl esters, or preferably less than 2% monounsaturated fatty acid alkyl esters.

In still other embodiments of the invention blends of fatty acid alkyl esters, the blends include less than 10% polyunsaturated fatty acid alkyl esters, preferably less than 7% polyunsaturated fatty acid alkyl esters, preferably less than 5% polyunsaturated fatty acid alkyl esters, preferably less than 3% polyunsaturated fatty acid alkyl esters, or preferably less than 1% polyunsaturated fatty acid alkyl esters.

In particular embodiments of the invention blends of fatty acid alkyl esters, the fatty acid alkyl esters are selected from the group consisting of methyl esters, ethyl esters, propyl esters, and butyl esters. In other embodiments the fatty acid alkyl esters are selected from the group consisting of iso-propyl ester, t-butyl ester, or sec-butyl ester. In preferred embodiments, the fatty acid alkyl esters are methyl esters. In some embodiments, caproic methyl ester (6:0) may be 0 to about 5% by weight of the total fatty acid methyl ester blend; caprylic methyl ester (8:0) may be about 5 to about 35%, or about 10 to about 30%, or about 15 to about 25% by weight of the total fatty acid methyl ester blend; capric methyl ester (10:0) may be about 20 to about 60%, or about 30 to about 50%, or about 40 to about 50% by weight of the total fatty acid methyl ester blend; lauric methyl ester (12:0) may be about 5 to about 30%, or about 10 to about 30%, or about 15 to about 25% by weight of the total fatty acid methyl ester blend; myristic methyl ester (14:0) may be 0 to about 5% by weight of the total fatty acid methyl ester blend; palmitic methyl ester (16:0) may be 0 to about 5% by weight of the total fatty acid methyl ester blend; palmitoleic methyl ester (16:1) may be 0 to about 10% by weight of the total fatty acid methyl ester blend; stearic methyl ester (18:0) may be 0 to about 5% by weight of the total fatty acid methyl ester blend; oleic methyl ester (18:1) may be 0 to about 10% by weight of the total fatty acid methyl ester blend; linoleic methyl ester (18:2) may be 0 to about 5% by weight of the total fatty acid methyl ester blend; linolenic methyl ester (18:3) may be 0 to about 1% by weight of the total fatty acid methyl ester blend; arachidic methyl ester (20:0) may be 0 to about 3% by weight of the total fatty acid methyl ester blend; behenic methyl ester (22:0) may be 0 to about 3% by weight of the total fatty acid methyl ester blend; erucic methyl ester (22:1) may be 0 to about 5% by weight of the total fatty acid methyl ester blend; and lignoceric methyl ester (24:0) may be 0 to about 3% by weight of the total fatty acid methyl ester blend.

In further embodiments of the above aspects of the invention, the blends of oils, or fatty acids, or fatty acid alkyl esters have a melting point of less than or equal to 0° C., preferably less than or equal to −10° C., preferably less than or equal to −15° C., preferably less than or equal to −20° C., or preferably less than or equal to −25° C.

In further embodiments of the above aspects of the invention, the blends of oils, or fatty acids, or fatty acid alkyl esters have a cloud point of less than or equal to 0° C., preferably less than or equal to −10° C., preferably less than or equal to −15° C., preferably less than or equal to −20° C., or preferably less than or equal to −25° C.

In further embodiments of the above aspects of the invention, the blends of oils, or fatty acids, or fatty acid alkyl esters have a pour point of less than or equal to 0° C., preferably less than or equal to −10° C., preferably less than or equal to −15° C., preferably less than or equal to −20° C., or preferably less than or equal to −25° C.

In some embodiments of the above aspects of the invention the blends of oils, or fatty acids, or fatty acid alkyl esters are suitable for use as a fuel in an internal combustion engine, as a fuel additive, a functional fluid, a freezing point depressant, a home heating oil, an aviation or jet fuel, or a substitute for kerosene.

The phrase "suitable for use in an internal combustion engine" refers to the properties of a fuel that enable it to be used to power an internal combustion engine. In some embodiments, a suitable fuel has a cetane number of 40-100; 40-80; or preferably 40-70; or preferably 40-60; or preferably 40-55; or preferably 40-50. In other embodiments a suitable fuel has an iodine number of 20-130; preferably 40-100; preferably 20-50, or preferably 10-20. In further embodiments, a suitable fuel has a melting point of less than or equal to 0° C., preferably less than or equal to −10° C., preferably less than or equal to −15° C., preferably less than or equal to −20° C., or preferably less than or equal to −25° C. In still further embodiments, a suitable fuel has a cloud point of less than or equal to 0° C., preferably less than or equal to −10° C., preferably less than or equal to −15° C., preferably less than or equal to −20° C., or preferably less than or equal to −25° C. In yet other embodiments, a suitable fuel has a pour point of less than or equal to 0° C., preferably less than or equal to −10° C., preferably less than or equal to −15° C., preferably less than or equal to −20° C., or preferably less than or equal to −25° C.

In other embodiments of the above aspect of the invention the blends of fatty acids or fatty acid alkyl esters are used as a biodiesel and are blended with petroleum-based diesel to form a biodiesel blend for use as a fuel. In particular embodiments, the biodiesel comprises 1%, 2%, 5%, 10%, 15%, 20%, 25%, 30%, 40%, 50%, or even 75% of the biodiesel blend, with petroleum-based diesel making up the remainder. The American Society for Testing Materials (ASTM) classifies two grades of diesel fuel, #1 diesel fuel and No. 2 diesel fuel. In particular embodiments, the biodiesel is blended with #1 diesel fuel, #2 diesel fuel, or is blended with a mixture of #1 and #2 diesel.

In another aspect, the invention features a genetically altered plant, wherein the plant expresses one or more modified enzymes having one or more mutations such that the plant produces increased quantities of medium chain fatty acids as compared to the native plant. In preferred embodiments, the genetically altered plant preferentially produces medium chain fatty acids having 8, 10, or 12 carbons. As used herein, the term "preferentially produces medium chain fatty acids having 8, 10, or 12 carbons" means that at least 50% by weight of the fatty acids produced by the genetically altered plant are medium chain fatty acids having 8, 10, or 12 carbons; more preferably at least 60%; more preferably at least 70%; more preferably at least 75%; more preferably at least 80%; more preferably at least 85%; more preferably at least 90%; more preferably at least 95%; more preferably at least 98% by weight of the fatty acids produced by the genetically altered plant are medium chain fatty acids having 8, 10, or 12 carbons.

In preferred embodiments of the above aspect of the invention, the genetically altered plant is derived from a plant which, in its native state produces an oil having greater than 40% long chain fatty acids. In some embodiments the genetically altered plant is derived from a native plant that is not a *Cuphea* species. *Cuphea* possesses certain traits that may be disadvantageous in certain embodiments of the invention. For example, "[w]ildtype *Cuphea* germplasm shatters and, as a consequence, cannot be commercially grown" (Knapp et al. "Modifying the seed storage of lipids of *Cuphea*: A source of medium chain triglycerides." In *Seed Oils for the Future*, 142-154, Champaign, Ill., AOCS Press). In addition, "it does not tolerate frost, the seeds shatter easily, flowering is unpredictable, and the stems, leaves and flowers are covered with sticky elastic hairs . . . [and] Germination is slow (14 to 20 days)" (Ag Innovation News, July-September 2003, Vol. 12, No. 3). Moreover, obtaining sufficient amounts of oil from *Cuphea* may hinder the ability to produce sufficient amounts of oil to make *Cuphea* commercially practical. However, in certain embodiments, certain other traits of *Cuphea* may provide an advantageous plant for modification. For example, "the plants grow quickly and seeds ripen in only six weeks, making it ideal for short-season temperate climates" (Ag Innovation News, July-September 2003, Vol. 12, No. 3).

Accordingly in certain embodiments a genetically altered *Cuphea* plant is provided that produces an oil blend of as disclosed herein.

In some embodiments of the above aspect of the invention, the plant expressing the modified enzyme is plant is selected from the group consisting of rapeseed, cotton, flax, peanut, palm, safflower, soybean, sunflower, castor, and corn. In preferred embodiments the plant is soybean, more preferably palm, or more preferably castor, or most preferably rapeseed. In particular embodiments the plant is a species of rapeseed, preferably *Brassica napus, Brassica juncea, Brassica rapa, Brassica oleracea, Brassica nigra, Brassica carinata*, and *Sinapis alba (Brassica alba Rabenh.)*.

In preferred embodiments of the above aspect of the invention, the mutation contained is introduced into the enzyme using a gene repair oligonucleobase containing the mutation.

A nucleobase comprises a base, which is a purine, pyrimidine, or a derivative or analog thereof. Nucleosides are nucleobases that contain a pentosefuranosyl moiety, e.g., an optionally substituted riboside or 2'-deoxyriboside. Nucleosides can be linked by one of several linkage moieties, which may or may not contain a phosphorus. Nucleosides that are linked by unsubstituted phosphodiester linkages are termed nucleotides. "Nucleobases" as used herein include peptide nucleobases, the subunits of peptide nucleic acids, and morpholine nucleobases as well as nucleosides and nucleotides.

An oligonucleobase is a polymer of nucleobases, which polymer can hybridize by Watson-Crick base pairing to a DNA having the complementary sequence. An oligonucleobase chain has a single 5' and 3' terminus, which are the ultimate nucleobases of the polymer. A particular oligonucleobase chain can contain nucleobases of all types. An oligonucleobase compound is a compound comprising one or more oligonucleobase chains that are complementary and hybridized by Watson-Crick base pairing. Nucleobases are either deoxyribo-type or ribo-type. Ribo-type nucleobases are pentosefuranosyl containing nucleobases wherein the 2' carbon is a methylene substituted with a hydroxyl, alkyloxy or halogen. Deoxyribo-type nucleobases are nucleobases other than ribo-type nucleobases and include all nucleobases that do not contain a pentosefuranosyl moiety.

An oligonucleobase strand generically includes both oligonucleobase chains and segments or regions of oligonucleobase chains. An oligonucleobase strand has a 3' end and a 5' end. When a oligonucleobase strand is coextensive with a chain, the 3' and 5' ends of the strand are also 3' and 5' termini of the chain.

The term "gene repair oligonucleobase" is used herein to denote oligonucleobases, including mixed duplex oligonucleotides, non-nucleotide containing molecules, single stranded oligodeoxynucleotides and other gene repair molecules as described in detail below.

In further embodiments of the above aspect of the invention, the enzyme which is modified is an acyl-ACP thioesterase. In certain embodiments, the modified acyl-ACP thioesterase is in a plant selected from the group consisting of rapeseed, cotton, flax, peanut, palm, safflower, soybean, sunflower, castor, and corn. In preferred embodiments the modified acyl-ACP thioesterase is in a variety of rapeseed, preferably *Brassica napus, Brassica juncea, Brassica rapa, Brassica oleracea, Brassica nigra, Brassica carinata, Sinapis alba (Brassica alba Rabenh.)*, preferably *Brassica napus*. In particular embodiments, the one or more mutations are contained within the region corresponding to amino acid residues 91-397 of SEQ ID NO:2; preferably the one or more designed mutations are contained in a region selected from the group consisting of amino acid residues 128-147 of SEQ ID NO:2, amino acid residues 175-206 of SEQ ID NO:2, amino acid residues 254-297 of SEQ ID NO:2, amino acid residues 333-335 of SEQ ID NO:2, or amino acid residues 365-397 of SEQ ID NO:2. In certain preferred embodiments the acyl-ACP thioesterase is palmitoyl-ACP thioesterase (PTE).

In still further embodiments of the above aspect of the invention, the enzyme which is modified is a keto acyl synthase (KAS). In particular embodiments the KAS enzyme may be modified so that its activity is decreased or eliminated. In other embodiments, the KAS enzyme may be modified so that it substrate selectivity is altered. In preferred embodiments, the KAS enzyme is KAS II and the one or more mutations are present at positions in a region corresponding to amino acid residues 328-385. In preferred embodiments the one or more mutations are present in the region corresponding to amino acid residues 325-352 of SEQ ID NO:3 or amino acid residues 355-385 of SEQ ID NO:3. In more preferred embodiments, one or more mutations are in the region corresponding to amino acid residues 325-340 of SEQ ID NO:3, or even amino acid residues 331-337 of SEQ ID NO:3. In some embodiments, the amino acid corresponding to the conserved leucine residue at position 337 of SEQ ID NO:3 is mutated.

In another aspect of the invention there are provided transgenic plants comprising two expressed transgenes encoding acyl-ACP thioesterases, wherein each thioesterase has an activity towards a different length medium chain fatty acids. Thus, such a transgenic plant will express both thioesterases and produce a blend of medium chain fatty acids.

In certain embodiments, the enzyme which is modified is $\Delta^9$-stearoyl acyl-ACP desaturase. In preferred embodiments the activity or expression of $\Delta^9$-stearoyl acyl-ACP desaturase is increased. In preferred embodiments, the increase of $\Delta^9$-stearoyl acyl-ACP desaturase activity in the genetically modified plant results in the genetically modified plant producing increased levels of C16:1 and/or C18:1; and/or decreased levels of C16:0 and/or decreased levels of C18:0 as compared to the native plant. In certain preferred embodiments, the of $\Delta^9$-stearoyl acyl-ACP desaturase gene is modified such that the genetically modified plant produces increased levels of C16:1. In certain embodiments the of $\Delta^9$-stearoyl acyl-ACP desaturase gene is modified such that it exhibits increased activity with palmitoyl-ACP; or in the genetically modified plant is a cotton, flax, peanut, palm, safflower, soybean, sunflower, *Cuphea*, castor or corn plant and the increased production of C16:0 is achieved by transformation of rapeseed with the $\Delta^9$-stearoyl acyl-ACP gene from macadamia (*Macadamia integrifolia*), sea buckthorn (*Hippophae rhamnoides*) or cat's claw (*Doxantha unguiscati*).

In certain embodiments, the enzyme that is modified is $\Delta 12$ desaturase (encoded by the FAD2 gene). In preferred embodiments the activity or expression of $\Delta 12$ desaturase is inhibited or attenuated. In preferred embodiments, the inhibition or attenuation of $\Delta 12$ desaturase activity or expression in the genetically modified plant results in the genetically modified plant producing decreased levels of C18:2, and/or C18:3; and increased levels of C18:1 relative to the native plant.

In certain embodiments of the above aspect, a first acyl-ACP thioesterase having activity towards C8 and C10 fatty acyl-ACP substrates and an expressed transgene encoding a second acyl-ACP thioesterase having activity towards C12 fatty acyl-ACP substrates. In a particular embodiment, the first acyl-ACP thioesterase is from a species of *Cuphea* and the second acyl-ACP thioesterase is from a species of *Ulmus*.

In certain aspects of the invention, a genetically modified plant is provided that is genetically modified such as to produce oil having a fatty acid mixture disclosed herein. For example in certain preferred embodiments a plant is provided that produces a mixture of fatty acids where saturated fatty acids having 8-12 carbons and monounsaturated fatty acids having 12-18 carbons account for between 80% and 100% of the mixture, caprylic acid (C8:0) and capric acid (C10:0) account for between 5% and 80% of the mixture, lauric acid accounts for less than 20% of the mixture, and polyunsaturated fatty acids and saturated fatty acids having more than 12 carbons together account for less than 20% of the mixture. In certain preferred embodiments of the genetically modified plant, the plant produces the aforementioned mixture of fatty acids wherein caprylic acid (C8:0), capric acid (C10:0), and lauric acid (C12:0) together account for 20% to 40% of the mixture; preferably lauric acid (C12:0) comprises 6% to 20% of the mixture, more preferably lauric acid (C12:0) comprises 6% to 10% of the mixture; and oleic acid (C18:1) and palmitoleic acid (16:1) together account for 50% to 85% of the mixture. In certain preferred embodiments of the genetically modified plant, the plant produces the aforementioned fatty acid mixture where caprylic acid (C8:0), capric acid (C10:0), and lauric acid (C12:0) together account for 60% to 85% of the mixture; preferably lauric acid (C12:0) comprises 6% to 20% of the mixture, more preferably lauric acid (C12:0) comprises 6% to 10% of the mixture; and oleic acid (C18:1) and palmitoleic acid (16:1) together account for 20% to 40% of the mixture. In a certain particularly preferred embodiment, a genetically modified plant is provided that produces an oil having about 10% C8; about 20% C10; about 10% C12; and about 60% C16:1 and/or C18:1. In a different particularly preferred embodiment, a genetically modified plant is provided that produces an oil having about 5% C8; about 5% C10; about 15% C12; about 70% C16:1 and/or C18:1; and about 1% or less of each of C14:0, C16:0, C18:0, C18:2 and C18:3.

In some embodiments of the above aspects of the invention, the genetically modified plant is generated from a plant selected from the group consisting of rapeseed, cotton, flax, peanut, *Cuphea*, safflower, soybean, sunflower, castor, and corn. In particular embodiments the plant is a variety of rapeseed, preferably *Brassica napus, Brassica juncea, Brassica rapa, Brassica oleracea, Brassica nigra, Brassica carinata*, and *Sinapis alba* (*Brassica alba* Rabenh.).

In certain particularly preferred embodiments of the above aspects, the genetically modified plant is a genetically altered plant; in other preferred embodiments, the genetically modified plant is a transgenic plant. Further embodiments are a plant that includes both transgenic and genetic alterations.

In one embodiment, the genetically modified plant is modified such that the genetically modified plant produces increased levels of medium chain fatty acids (preferably increased levels of C8:0, C10:0 and C12:0 in accordance with preferred fatty acid blends provided herein) and/or decreased levels of palmitic acid (C16:0) and/or decreased levels of C18:0. In other preferred embodiments, the genetically modified plant is modified such that it produces increased levels of monounsaturated fatty acids, preferably increased levels of C16:1 and C18:1 monounsaturated fatty acids; and produces lower levels of saturated and polyunsaturated fatty acids, preferably lower levels of C16:0, C18:0, C18:2 and/or C18:3. In particularly preferred embodiments the genetically modified plant is modified to produce increased levels of medium chain fatty acids (preferably increased levels of C8:0, C10:0 and/or C12:0); decreased levels of C16:0 and C18:0; and increased levels of C16:1 and C18:1.

In one particularly preferred embodiment of the above aspects, a rapeseed plant is provided that is genetically modified to produce an oil having a fatty acid mixture provided herein. In certain preferred embodiments the genetically modified rapeseed plant is modified such that, relative to a native rapeseed plant, the genetically modified rapeseed plant produces increased levels of medium chain fatty acids (preferably increased levels of C8:0, C10:0 and C12:0 in accordance with preferred fatty acid blends provided herein) and/or decreased levels of palmitic acid (C16:0) and/or decreased levels of C18:0. In other preferred embodiments, the genetically modified rapeseed plant is modified such that, relative to a native rapeseed plant, the genetically modified rapeseed plant produces increased levels of monounsaturated fatty acids, preferably increased levels of C16:1 and C18:1 monounsaturated fatty acids, and produces lower levels of saturated and polyunsaturated fatty acids, preferably lower levels of C16:0, C18:0, C18:2 and C18:3. In particularly preferred embodiments the genetically modified rapeseed plant is modified to produce increased levels of medium chain fatty acids (preferably increased levels of C8:0, C10:0 and/or C12:0); decreased levels of C16:0 and C18:0; and increased levels of C16:1 and/or C18:1.

In another particularly preferred embodiment of the above aspects, a soy plant is provided that is genetically modified to produce an oil having a fatty acid mixture provided herein. In certain preferred embodiments the genetically modified soy plant is modified such that, relative to a native soy plant, the genetically modified soy plant produces increased levels of medium chain fatty acids (preferably increased levels of C8:0, C10:0 and C12:0 in accordance with preferred fatty acid blends provided herein) and/or decreased levels of palmitic acid (C16:0) and/or decreased levels of C18:0. In other preferred embodiments, the genetically modified soy plant is modified such that, relative to a native soy plant, the genetically modified soy plant produces increased levels of monounsaturated fatty acids, preferably increased levels of C16:1 and C18:1 monounsaturated fatty acids, and produces lower levels of saturated and polyunsaturated fatty acids, preferably lower levels of C16:0, C18:0, C18:2 and C18:3. In particularly preferred embodiments the genetically modified soy plant is modified to produce increased levels of medium chain fatty acids (preferably increased levels of C8:0, C10:0 and/or C12:0); decreased levels of C16:0 and C18:0; and increased levels of C16:1 and/or C18:1.

In further embodiments of the above aspects of the invention there are provided seeds for producing the genetically altered or transgenic plants.

In still further embodiments of the above aspects of the invention there are provided oils or fatty acid mixtures extracted from the seed, fruit, or leaves of the above genetically altered or transgenic plants.

In another aspect of the invention there are provided methods of producing a biodiesel from an oil obtained from an altered plant or a transgenic plant. In certain embodiments an oil from a genetically altered plant or a transgenic plant is used as the only oil in making a biodiesel. In other embodiments, an oil from a genetically altered plant is blended with an oil from a native plant, a transgenic plant, or both and used in the making of a biodiesel. In particular embodiments the oil is derived from a genetically altered plant in which one or more mutations has been introduced using gene repair oligonucleobases, such oils may be used alone or in combination with one or more oils obtained from a transgenic plant or native plant or other genetically altered plant. In certain embodiments, the method comprises transesterifying the oil extracted from the seed, fruit, or leaves one or more genetically altered plants or transgenic plants blended with the oil obtained from one or more native plants to produce a biodiesel containing fatty acid alkyl esters. In some embodiments, transesterifying is accomplished by reacting said oil with an alcohol and a base catalyst. In further embodiments, the method further includes purifying the fatty acid alkyl esters, such purifying can include the removal of catalyst, glycerin, and water.

In still other embodiments an oil from a transgenic plant is blended with one or more oils from a genetically altered plant, a native plant, or both and used in the making of a biodiesel. In particular embodiments, the transgenic plant expresses one or more transgenes. In particular embodiments the transgene express a protein that alters the content of the medium chain fatty acids produced by the plant. In preferred embodiments the transgenic plant produces higher amounts of medium chain fatty acids than the native plant. In more preferred embodiments, the transgenic plant preferentially produces medium chain fatty acids having 8, 10, or 12 carbons. In more preferred embodiments the transgenic plant produces an oil having less long chain fatty acids than the native plant.

In still another aspect of the invention there is provided a method for predicting a theoretical melting point of a blend of fatty acid methyl esters. This method computes the sum of the product of: the percent (w/w) of an individual fatty acid methyl ester (X), the melting point for that ester ($MP_x$), and a factor ($F_x$), for each fatty acid ME contained in the blend. Thus, there is a term for each methyl ester corresponding to, for example, ($X*MP_x*F_x$). The numerical definitions of the melting points and factors used in the method can be varied and still produce a valid intermediate value. The term "factor" as used herein refers to a constant value corresponding to a fatty acid methyl ester. The factor is multiplied with the percent content for that fatty acid ME and the melting point for that fatty acid ME to produce a term for that fatty acid ME that is used in the method. For example, individual melting points can vary by plus or minus 2° C., or 5° C., or even 10° C. and the individual factors may vary by 5% or 10% or even 20% and still produce a valid predicted melting temperature for the blend.

In certain embodiments, there is provided a method of predicting the melting point of a blend wherein the predicted melting point, $P_{Tm}$, is computed as follows:

$$P_{Tm} = [(A*MP_A*F_A) + (B*MP_B*F_B) + (C*MP_C*F_C) + (D*MP_D*F_D) + (E*MP_E*F_E) + (F*MP_F*F_F) + (G*MP_G*F_G) + (H*MP_H*F_H) + (I*MP_I*F_I) + (J*MP_J*F_J) + (K*MP_K*F_K) + (L*MP_L*F_L) + (M*MP_M*F_M)]*(0.01),$$

wherein,

A is the percent (w/w) caproic ME (6:0) in the blend;
B is the percent (w/w) caprylic ME (8:0) in the blend;
C is the percent (w/w) capric ME (10:0) in the blend;
D is the percent (w/w) lauric ME (12:0) in the blend;
E is the percent (w/w) myristic ME (14:0) in the blend;
F is the percent (w/w) palmitic ME (16:0) in the blend;
G is the percent (w/w) stearic ME (18:0) in the blend;
H is the percent (w/w) oleic ME (18:1) in the blend;
I is the percent (w/w) linoleic ME (18:2) in the blend;
J is the percent (w/w) linolenic ME (18:3) in the blend;
K is the percent (w/w) arachidic ME (20:0) in the blend;
L is the percent (w/w) behenic ME (22:0) in the blend;
M is the percent (w/w) lignoceric ME (24:0) in the blend;
$MP_A$ is −81° C. to −61° C. inclusive;
$MP_B$ is −50° C. to −30° C. inclusive;
$MP_C$ is −28° C. to −8° C. inclusive;
$MP_D$ is −5° C. to 15° C. inclusive;
$MP_E$ is 9° C. to 29° C. inclusive;
$MP_F$ is 21° C. to 41° C. inclusive;
$MP_G$ is 28° C. to 48° C. inclusive;
$MP_H$ is −30° C. to −10° C. inclusive;
$MP_I$ is −45° C. to −25° C. inclusive;
$MP_J$ is −67° C. to −47° C. inclusive;
$MP_K$ is 45° C. to 65° C. inclusive;
$MP_L$ is 43° C. to 63° C. inclusive;
$MP_M$ is 48° C. to 68° C. inclusive;
$F_A$ is 8 to 12 inclusive;
$F_B$ is 3.5 to 5.5 inclusive;
$F_C$ is 1.0 to 1.4 inclusive;
$F_D$ is 0.8 to 1.2 inclusive;
$F_E$ is 0.5 to 0.7 inclusive;
$F_F$ is 1.1 to 1.6 inclusive;
$F_G$ is 1.8 to 2.6 inclusive;
$F_H$ is 0.9 to 1.3 inclusive;
$F_I$ is 0.5 to 0.8 inclusive;
$F_J$ is 0.15 to 0.25 inclusive;
$F_K$ is 8 to 12 inclusive;
$F_L$ is 1.6 to 2.4 inclusive; and
$F_M$ is 1.6 to 2.4 inclusive.

In a particular embodiment of the above aspect of the invention, the predicted melting point is computed as follows:

$$P_{Tm} = [A(-71.0)(10.0) + B(-40.0)(4.5) + C(-18.0)(1.2) + D(5.2)(1.0) + E(19.0)(0.60) + F(30.7)(1.35) + G(37.8)(2.15) + H(-19.9)(1.10) + I(-35.0)(0.65) + J(-57)(0.2) + K(54.5)(10.0) + L(53.0)(2.0) + M(57.4)(2.0)]*(0.01),$$

and A through M are defined as above.

In a related embodiment of the above aspect, the algorithm is used to identify blends of fatty acid methyl esters that are suitable for use as a biodiesel wherein the predicted melting point of the blend is computed and compared to a cut-off value. The "cut-off value" as used herein refers to a desired melting point, wherein blends having a $P_{Tm}$ less than or equal to that desired melting point are suitable for use as a biodiesel. In particular embodiments, the cut-off value is 0° C., preferably −5° C., preferably −10° C., preferably −15° C., preferably −20° C., preferably 0° C., or preferably −20° C.

The term "percent by weight" as used herein refers to the amount of a component in a blend or mixture. In general this refers to grams of a component per 100 grams of a mixture. For example a mixture having "10% compound X by weight" refers to 10 grams of compound X in 100 grams of the mixture.

The term "biodiesel" as used herein, refers to a fuel derived from vegetable oil or animal fat. In general, a biodiesel is composed of primarily fatty acid alkyl esters. Preferably, a biodiesel is suitable for use in an internal combustion engine.

The term "biodiesel blend" refers to a fuel that is a blend of a biodiesel and another fuel. In general, biodiesels are blended with a petroleum-based fuel (i.e., petrodiesel). Biodiesel blends are referred to as BXX. The "XX" indicates the amount of biodiesel in the blend. B100 is 100% biodiesel or "neat" biodiesel. A B20 blend, for example, is a 20% volumetric blend of biodiesel with 80% petrodiesel.

The term "fuel" refers to a substance that is burned to give heat or power. Examples include liquids such as gasoline, home heating oil, aviation fuel, kerosene, diesel, biodiesel, vegetable oil, and biodiesel blends. Some fuels, for example, gasoline, diesel, biodiesel, vegetable oil, or biodiesel blends can be used to power an internal combustion engine.

The phrase "genetically modified plant" refers to a transgenic plant or a genetically altered plant.

The term "native plant" as used herein refers to a plant that is not genetically modified (i.e., transgenic or genetically altered). Native plants include wild type plants as well as plants that have been selectively bred to attain particular characteristics.

The phrase "transgenic plant" refers to a plant having a gene from another plant species or non-plant species. Such a gene may be referred to as a "transgene."

The phrase "genetically altered plant" refers to a plant having one or more genetic modifications, such as transgenes and/or modified enzymes which contain one or more designed mutation(s). Such designed mutations may result in a modified enzyme having an activity that is different from the native enzyme. Such differences can include differences in substrate specificity or level of activity. As used herein, a "transgenic plant" is one type of a "genetically altered plant".

The phrase "fuel additive" refers to a liquid substance that is added to a fuel, comprising less than 5% weight of the final fuel.

The phrase "mixture of fatty acids" or "blend of fatty acids" or "fatty acid blend" may be used interchangeably and refer to a composition that includes various fatty acids. In certain embodiments a mixture of fatty acids may be an oil or blend of oils, in other embodiments a mixture of fatty acids may be a mixture of free fatty acids or a mixture of free fatty acids and an oil or blend of oils. In certain embodiments some or all of the fatty acids in a mixture of fatty acids may be modified to form fatty acid alkyl esters, for example fatty acid methyl esters, fatty acid ethyl esters, fatty acid propyl esters and the like. In certain preferred embodiments, the fatty acid alkyl esters include methyl esters. Accordingly, unless otherwise indicated the phrase "mixture of fatty acids" as used herein encompasses mixtures of fatty acid alkyl esters of the fatty acids specified in the mixture. Likewise, unless otherwise indicated, the term "fatty acid" as used herein includes alkyl esters of the fatty acid.

The phrase "functional fluid" refers to a liquid substance added to a fuel, comprising more than 5% weight of the final fuel.

The phrase "freezing point depressant" refers to a liquid substance added to a fuel to lower the freezing point of that fuel.

The "cetane number" or CN is a measure of fuel ignition characteristics and correlates to the ignition delay period. For example, a fuel with a high cetane number starts to burn shortly after it is injected into the cylinder (i.e., it has a short ignition delay period). Conversely, a fuel with a low cetane number has a longer ignition delay period. Further, a higher cetane number correlates with improved combustion, improved cold starting, reduced noise, reduced white smoke, and reduced emissions of HC, CO and particulate, particularly during early warm-up phase. Commercially available petroleum-derived diesel is generally found in two CN ranges: 40-46 for regular diesel, and 45-50 for premium.

The "iodine number" is determined through a standard natural oil assay to measure the degree of unsaturation in vegetable oils and fats.

The "cloud point" refers to the temperature at which the first wax crystals appear and a standardized test protocol from the American Society for Testing and Materials (ASTM) is used to determine this temperature.

The "pour point" refers to the temperature at which the fuel will no longer pour. The pour point is generally lower than the cloud point. Some engines will fail to run at the cloud point, but generally all engines will fail at the pour point.

The "melting point" of a crystalline solid refers to the temperature at which it changes state from solid to liquid. When considered as the temperature of the reverse change (i.e., from liquid to solid), it is referred to as the "freezing point." For most substances, the melting and freezing points are equal. The melting point or freezing point is lower than the pour point.

"Feedstock" as used herein refers to a substance composed of fats, fatty acids, or triglycerides that may be used as a starting material for the preparation of a biodiesel. Examples of feedstocks which may be used in the production of biodiesels include vegetable oil, waste vegetable oil, and animal fats. Other feedstocks include mixtures of fatty acids or fatty acid alkyl esters.

The term "about" as used herein means in quantitative terms plus or minus 10%. For example, "about 3%" would encompass 2.7-3.3% and "about 10%" would encompass 9-11%.

Unless otherwise indicated, any percentages stated herein are percent by weight.

Other features and advantages of the invention will be apparent from the following description of the preferred embodiments and from the claims.

BRIEF DESCRIPTION OF THE FIGURES

FIG. 1 shows a partial amino acid sequence (SEQ ID NO:1) of the acyl-ACP thioesterase (palmitoyl-ACP thioesterase or PTE) from *Brassica napus*.

FIG. 2 shows the amino acid sequence (SEQ ID NO:2) of the acyl-ACP thioesterase (palmitoyl-ACP thioesterase or PTE) from *Arabidopsis*.

FIG. 3 shows the amino acid sequence (SEQ ID NO:3) of the keto acyl synthase II (KAS II) from *Arabidopsis thaliana* (GenBank Accession No. NP_849888).

FIG. 4 shows the nucleotide sequence (SEQ ID NO:4) of the keto acyl synthase II (KAS II) from *Arabidopsis thaliana* (GenBank Accession No. NM_179557).

FIG. 6 shows the fatty acid content of some exemplary oils.

DETAILED DESCRIPTION OF THE INVENTION

Blending Oils

Figure 5:
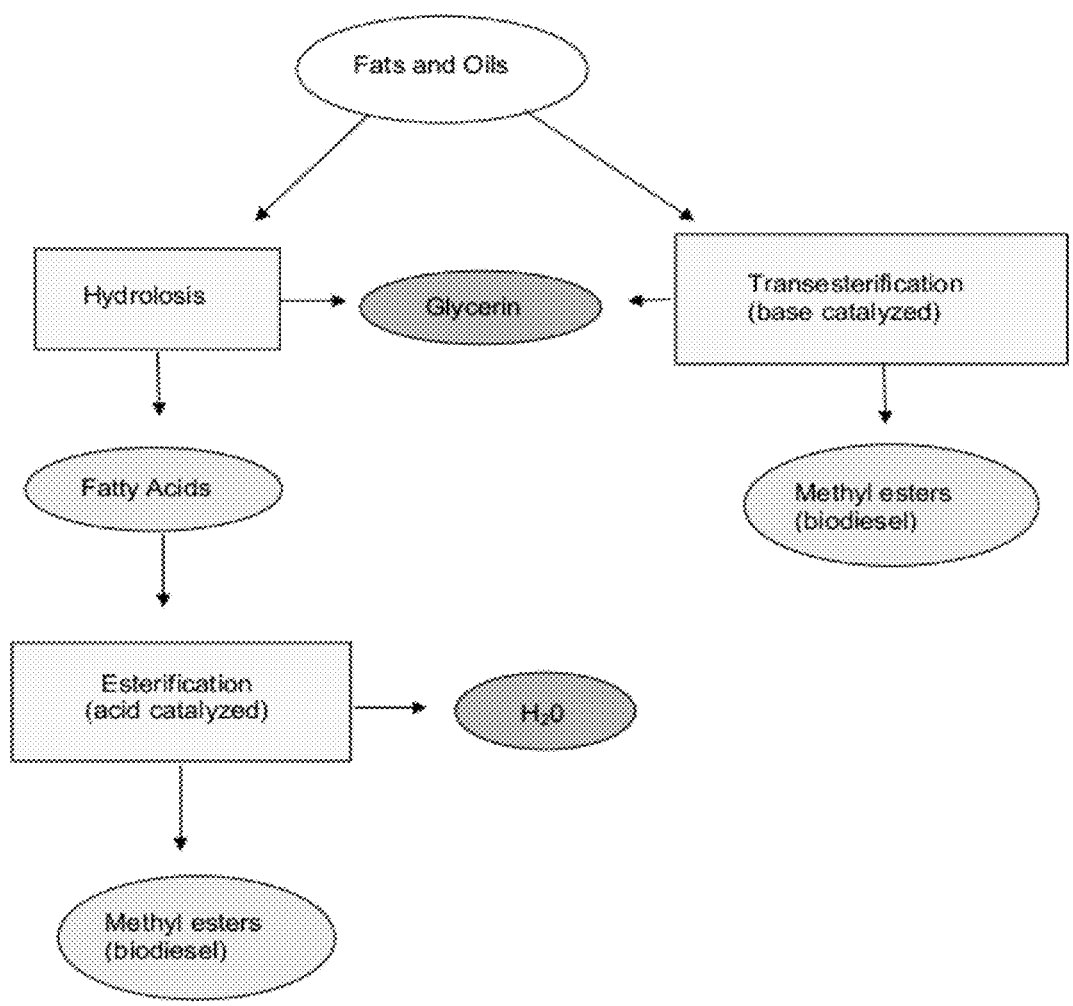
FIG. 5 shows two pathways by which a biodiesel can be produced from an oil or fat.

Oils containing various compositions of medium chain fatty acids may be blended in order to achieve a desired blend of medium chain fatty acids. Oils are blended on a by weight basis. For example, the volume of rapeseed oil to be used in 100 grams of a blend composed of 25% rapeseed oil is determined by dividing the grams of rapeseed oil in the final blend by the specific gravity of rapeseed oil (i.e., 25 gm/0.915 gm/mL=27.3 mL).

FIG. 6 is a table containing some exemplary oils and the fatty acid content contained therein. These oils are commercially available from a variety of sources. It is noted that the fatty acid content values are expressed as ranges, because, as it is known in the art, the amounts of particular fatty acids present in a particular plant, can vary significantly. Thus, oils extracted from those plants may exhibit differing quantities of any or all fatty acids from batch to batch. Therefore, it is normally necessary to determine the fatty acid content of the oils actually used to make blends or a biodiesel.

Preparation of Fatty Acid Alkyl Esters

Fatty acid alkyl esters can be produced from fatty acids or from triglycerides. Generally, fatty acid alkyl esters are produced by transesterification of the triglycerides in fats and oils or esterification of free fatty acids (FIG. 5). Alternatively, fatty acids may be split from triglycerides through hydrolysis and subsequently subjected to esterification to produce the fatty acid ester.

Fatty acid alkyl esters may be prepared by a transesterification reaction of the triglycerides found in various plant-derived oils such as soybean oil, palm oil, safflower oil, peanut oil, corn oil, cottonseed oil, linseed oil, coconut oil, castor oil, rapeseed oil, sunflower oil, and various oils derived from animal fats. These oils are reacted with an alcohol (e.g., methanol, ethanol, propanol, butanol) in the presence of a base catalyst such as a sodium alkoxide, sodium or potassium hydroxide, or titanium tetraisopropoxide. Reaction conditions such as temperature and pressure can be selected based on the specific alcohol used. The amount of catalyst is generally in the range of from about 0.1 to about 0.5% by weight based on the fatty acid. This process produces a fatty acid alkyl ester, wherein the alkyl group is derived from the alcohol. Thus, a reaction in which methanol was used as the alcohol would yield a fatty acid methyl ester. Other by-products include glycerin. The transesterification products are isolated by reduced pressure fractionation by distillation through a fractionation column.

Fatty acid alkyl esters may be prepared from free fatty acids through esterification. Free fatty acids are commercially available from a number of sources or may be derived from, for example, the aforementioned oils, can be reacted with an alcohol in the presence of an acid catalyst such as sulfuric acid, aryl sulfonic acids, or alkyl sulfonic acids. Reaction conditions such as temperature and pressure can be selected based on the specific alcohol used. The fatty acid esters can be recovered by neutralizing the sulfuric acid, and subsequent purification to remove aqueous constituents of the reaction.

Blending Fatty Acid Esters

Fatty acid esters are commercially available or can be obtained by esterification of the fatty acid as described above. Fatty acids are blended in order to achieve a mixture having suitable properties for use as a biodiesel, fuel additive, functional fluid, aviation or jet fuel, home heating oil, or kerosene. The properties to consider in evaluating blends can include melting point, cloud point, pour point, iodine number, cetane number, viscosity, oxidative stability, and frictional wear characteristics.

Blends are made on a weight percent basis. For a blend of fatty acid methyl esters (FAMEs), the desired weight percent of each component FAME is divided by the specific gravity of that FAME. This yields the volume of the FAME per 100 grams of final blend. For example, to achieve a blend containing 14% (wt %) of capric acid methyl ester (having a specific gravity of 0.877 g/mL), the volume of capric acid methyl ester to be used in making 100 grams of the final blend is determined as follows.

Volume of capric acid methyl ester=(14 g/0.877 g/mL)=15.96 ml

Thus, 15.96 ml of capric acid methyl ester would be required for each 100 gm of final blend.

Determination of the weight percent of a blend of FAMEs or the FAME mixture resulting from the conversion of the fatty acids contained in an oil blend to fatty acid esters is performed using a capillary gas chromatograph (Agilent Model 6890) (column-Supelco SPB-225, 30 M×0.32 mm, 0.25 µm film thickness) equipped with a flame ionization detector (FID). Sample peak areas are compared with peak areas of a known weight of calibrated standard FAME for each peak to determine the weight of each FAME in the sample. All weights are summed and the ratio of the individual FAME weight to the total (after conversion to percent) is the weight percent.

Melting point. A low melting point of a blend of fatty acid esters is desirable to avoid freezing when such a blend is used in colder climates. Means of achieving a low melting point of a blend of fatty acid methyl esters have generally involved blending with conventional diesel fuel, inclusion of additives having branched-chain esters, and/or bulky substituents in the alkyl chain, and/or winterization of the blend. Blends of the present invention achieve a low melting point through the inclusion of medium chain fatty acid methyl esters, particularly C8 and C10 methyl esters. Thus, fatty acid esters may be blended to achieve a particular melting point and the melting point of the resulting blend can be determined.

The melting point can be determined by methods well-known in the art. In one method, the melting point of a blend of fatty acid methyl esters is determined by placing an aliquot of the blend in a closed end glass capillary tube and equilibrating the tube in a water bath or ethylene glycol bath held at a temperature that is below the expected melting point of the blend. After a period of time sufficient to allow the tube and its contents to equilibrate, the temperature of the water bath is raised slowly. The tube is observed by eye or using a light scattering instrument (spectrophotometer). The temperature at which the transition from solid to liquid is observed or at which light scattering diminishes is recorded as the melting point of the sample.

An alternative to a simple melting point, as explained above, is a "slip melting point". In this method, a small amount of sample is placed in a closed end capillary such that the sample is suspended in the center of the tube lengthwise. After equilibration in a water bath, the temperature is slowly raised and the temperature at which the suspended sample just begins to fall or "slip" in the capillary is recorded as the slip melting point.

Determination of melting point of a solid fat is also detailed in methods proscribed by the American Association of Cereal Chemists (AACC) method number 58-40 "Melting Point-Capillary Method, and method number 58-53 Slip Melting point. In addition, methods are also available from the American Oil Chemists Society (AOCS) Official Method Cc 1-25 "Melting Point Capillary Tube Method" and AOCS Official Method Cc 3-25 "Slip Melting Point AOCS Standard Open Tube Melting Point".

Alternatively, a predicted melting point can be computed using the algorithm contained herein.

Cloud point and pour point. Cloud point and pour point may be determined in the same experiment using a single apparatus. Briefly, the sample is cooled in a cloud and pour point apparatus and is examined periodically during cooling. The highest temperature at which haziness is observed is the cloud point. The lowest temperature at which movement of the oil is observed is the pour point. This method should conform to ASTM D97, D2500 and related specifications. Such an apparatus (K46100 Cloud Point & Pour Point Apparatus Cloud and Pour Point Chamber) is available from Koehler Instrument Company, Inc., 1595 Sycamore Avenue, Bohemia, N.Y. 11716, USA.

Cetane number. The ignition quality of diesel fuel (DF) is commonly measured by the American Society for Testing and Materials (ASTM) test method ASTM D613 and reported as the cetane number (CN). Ignition quality is defined by the ignition delay time of the fuel in the engine. The shorter the ignition delay time, the higher the CN. Compounds are ranked according to the cetane scale. Cetane ($C_{16}H_{34}$ or hexadecane) has a very short ignition delay and has been assigned a CN of 100. At the other end of the scale is 2,2,4,4,6,8,8-heptamethylnonane (HMN; also $C_{16}H_{34}$), which has poor ignition qualities and has been assigned a CN of 15. In general, long-chain, unbranched, saturated hydrocarbons (alkanes) have high CNs and good ignition quality while branched hydrocarbons (and other materials such as aromatics) have low CNs and poor ignition quality. Further, the presence of double bonds or degrees of unsaturation in a fatty acid will lower cetane value.

Since both too high and too low CN can cause operational problems (in case of too high CN, combustion can occur before the fuel and air are properly mixed, resulting in incomplete combustion and smoke; in case of too low CN, engine roughness, misfiring, higher air temperatures, slower engine warm-up and also incomplete combustion occur), most engine manufacturers designate a range of required CN for their engines. In most cases, this range is around CN 40-50. For example, the ASTM specification for conventional diesel fuel (ASTM D975) requires a minimum CN of 40.

Iodine number. The iodine number is a commonly used measure of saturation and therefore, an indicator of oxidative stability. As mentioned earlier, unsaturated molecules are more susceptible to oxidation than saturated molecules. This test uses iodine to measure the number of double bonds in an oil or fuel. Thus, oils with high iodine numbers, such as soybean oil (IN=130-135) are very susceptible to oxidation while animal fats with low iodine numbers, such as tallow (IN=30-48) are much less susceptible. The primary drawback of the iodine number is that it does not recognize that some double bonds oxidize more readily than others. Methyl linoleate, with two double bonds, will oxidize approximately 50 times faster than methyl oleate, with only one double bond. Methyl linolenate, with three double bonds, will oxidize even faster, although not by the same level of increase. Thus, blends of primarily saturated, medium chain fatty acids would be expected to have low iodine numbers, and therefore exhibit good oxidative stability.

Production of a Genetically Altered Plant that Produces Oils with Altered Fatty Acid Compositions.

U.S. Pat. No. 6,150,512 discloses that "[m]ethods of altering substrate specificity of plant acyl-ACP thioesterases, and engineered plant acyl-ACP thioesterases so produced are provided," in particular, "a mangosteen Garm FatA1 18:1 thioesterase in which the relative 18:0 activity has been increased."

U.S. Pat. No. 5,955,329 discloses "[m]ethods of altering substrate specificity of plant acyl-ACP thioesterases, and engineered plant acyl-ACP thioesterases." In particular, it is disclosed that "[a] C12 preferring plant acyl-ACP thioesterase described herein may be altered to obtain a plant thioesterase having approximately equal activity on C14 and C12 substrates."

Carlsson et al. (Plant Journal 29(6):761-770, 2002) disclose a "a fab1 mutant of *Arabidopsis* [that] is partially deficient in activity of β-ketoacyl-[acyl carrier protein] synthase II (KASII)." The fab1 mutation is described as "a single nucleotide change in sequence in *Arabidopsis* KAS2 that results in a Leu337Phe substitution."

Knapp et al. ("Modifying the seed storage of lipids of *Cuphea*: A source of medium chain triglycerides." In *Seed Oils for the Future*, 142-154, Champaign, Ill., AOCS Press) disclose mutant *Cuphea viscosissima*, created by random mutagenesis, that produce oils having altered triglyceride compositions.

U.S. Pat. Nos. 5,667,997, 5,455,167, 5,298,421 and 5,512,482 disclose the nucleotide and amino acid sequences of acyl-ACP thioesterases having specificity for medium chain fatty acids and corresponding transgenic plants expressing each of these thioesterases.

A genetically altered plant producing medium chain fatty acids may be produced by mutating or modifying one or more enzymes within the fatty acid biosynthesis pathway. Fatty acid biosynthesis occurs in the plastid of plants. The synthesis of fatty acids progresses from a two-carbon precursor, bound to an acyl protein carrier (ACP), via sequential two-carbon addition in a reaction catalyzed by the enzyme keto acyl synthase (KAS). During this process the fatty acid remains esterified to the ACP, resulting in pools of acyl-ACP intermediates in which the acyl portion is of varying length. Thioesterases present in the plastid hydrolyze the thiol-ester linkage between the fatty acid and the ACP, thus releasing the fatty acid which can then exit the plastid and be assembled into triglycerides.

Several isomers of KAS having affinities for acyl chains of particular lengths. For example, KAS I enzyme of, for example, *Brassica napus*, has little affinity for acyl chains longer than 16 carbons, thus this enzyme would not elongate an acyl chain beyond 16 carbons. KAS II specifically catalyzes the reaction to elongate acyl chains of 16 carbons to acyl chains of 18 carbons. KAS II has little affinity for acyl chains longer or shorter than 16 carbons.

Similarly, acyl-ACP thioesterases have been identified having preferential activity for acyl chains of specific lengths. There are, for example, thioesterases that primarily hydrolyze acyl-ACPs having fatty acids of 18 carbons (e.g., oleoyl-ACP thioesterase or OTE). Similarly, there are thioesterases having preferential activity for acyl-ACPs having fatty acids of 16 carbons (e.g., palmitoyl-ACP thioesterase or PTE). Further, thioesterases having preferential activity for various medium chain fatty acids have been reported. "Preferential activity" of a plant thioesterase toward a particular chain-length fatty acyl-carrier substrate is determined upon comparison of free fatty acid product amounts obtained per different chain length substrates. For example, by "C12-preferring" is meant that the hydrolytic activity of the enzyme preparation demonstrates a preference for lauroyl, and perhaps decanoyl, over other substrates of different acyl carbon lengths. Similarly, a plant thioesterase having "C10-preferring" activity will show higher levels of activity toward decanoyl substrates, and perhaps octanoyl, over other substrates of different carbon lengths. It is noted that some activity, of a significantly lesser magnitude, may be observed for other chain-length fatty acyl substrates. Thus, the preference may be substantial, but may not be absolute.

In preferred embodiments, the genetically altered plant expressing a modified enzyme is produced by introducing a mutation in the enzyme through use of a gene repair oligonucleobase as described herein. The method comprises introducing a gene repair oligonucleobase containing a specific mutation for target gene of interest into a plant cell by any of a number of methods well-known in the art (e.g., microcarriers, microfibers, electorporation, and microinjection) and identifying a cell, seed or plant having the mutated enzyme.

As used herein the term "target gene" refers to the gene encoding the enzyme to be modified.

Gene Repair Oligonucleobases

The invention can be practiced with "gene repair oligonucleobases" having the conformations and chemistries as described in detail below. The "gene repair oligonucleobases" of the invention include mixed duplex oligonucleotides, non-nucleotide containing molecules, single stranded oligodeoxynucleotides and other gene repair molecules described in the below noted patents and patent publications. The "gene repair oligonucleobases" of the invention have also been described in published scientific and patent literature using other names including "recombinagenic oligonucleobases;" "RNA/DNA chimeric oligonucleotides;" "chimeric oligonucleotides;" "mixed duplex oligonucleotides (MDONs);" "RNA DNA oligonucleotides (RDOs);" "gene targeting oligonucleotides;" "genoplasts;" "single stranded modified oligonucleotides;" "Single stranded oligodeoxynucleotide mutational vectors;" "duplex mutational vectors;" and "heteroduplex mutational vectors."

Oligonucleobases having the conformations and chemistries described in U.S. Pat. No. 5,565,350 by Kmiec (Kmiec I) and U.S. Pat. No. 5,731,181 by Kmiec (Kmiec II), hereby incorporated by reference, are suitable for use as "gene repair oligonucleobases" of the invention. The gene repair oligonucleobases in Kmiec I and/or Kmiec II contain two complementary strands, one of which contains at least one segment of RNA-type nucleotides (an "RNA segment") that are base paired to DNA-type nucleotides of the other strand.

Kmiec II discloses that purine and pyrimidine base-containing non-nucleotides can be substituted for nucleotides. Additional gene repair molecules that can be used for the present invention are described in U.S. Pat. Nos. 5,756,325; 5,871,984; 5,760,012; 5,888,983; 5,795,972; 5,780,296; 5,945,339; 6,004,804; and 6,010,907 and in International Patent No. PCT/US00/23457; and in International Patent Publication Nos. WO 98/49350; WO 99/07865; WO 99/58723; WO 99/58702; and WO 99/40789, which are each hereby incorporated in their entirety.

In one embodiment, the gene repair oligonucleobase is a mixed duplex oligonucleotide in which the RNA-type nucleotides of the mixed duplex oligonucleotide are made RNase resistant by replacing the 2'-hydroxyl with a fluoro, chloro or bromo functionality or by placing a substituent on the 2'-O, Suitable substituents include the substituents taught by the Kmiec II. Alternative substituents include the substituents taught by U.S. Pat. No. 5,334,711 (Sproat) and the substituents taught by patent publications EP 629 387 and EP 679 657 (collectively, the Martin Applications), which are hereby incorporated by reference. As used herein, a 2'-fluoro, chloro or bromo derivative of a ribonucleotide or a ribonucleotide having a 2'-OH substituted with a substituent described in the Martin Applications or Sproat is termed a "2'-Substituted Ribonucleotide." As used herein the term "RNA-type nucleotide" means a 2'-hydroxyl or 2'-Substituted Nucleotide that is linked to other nucleotides of a mixed duplex oligonucleotide by an unsubstituted phosphodiester linkage or any of the non-natural linkages taught by Kmiec I or Kmiec II. As used herein the term "deoxyribo-type nucleotide" means a nucleotide having a 2'-H, which can be linked to other nucleotides of a gene repair oligonucleobase by an unsubstituted phosphodiester linkage or any of the non-natural linkages taught by Kmiec I or Kmiec II.

In a particular embodiment of the present invention, the gene repair oligonucleobase is a mixed duplex oligonucleotide that is linked solely by unsubstituted phosphodiester bonds. In alternative embodiments, the linkage is by substituted phosphodiesters, phosphodiester derivatives and non-phosphorus-based linkages as taught by Kmiec II. In yet another embodiment, each RNA-type nucleotide in the mixed duplex oligonucleotide is a 2'-Substituted Nucleotide. Particular preferred embodiments of 2'-Substituted Ribonucleotides are 2'-fluoro, 2'-methoxy, 2'-propyloxy, 2'-allyloxy, 2'-hydroxylethyloxy, 2'-methoxyethyloxy, 2'-fluoropropyloxy and 2'-trifluoropropyloxy substituted ribonucleotides. More preferred embodiments of 2'-Substituted Ribonucleotides are 2'-fluoro, 2'-methoxy, 2'-methoxyethyloxy, and 2'-allyloxy substituted nucleotides. In another embodiment the mixed duplex oligonucleotide is linked by unsubstituted phosphodiester bonds.

Although mixed duplex oligonucleotides having only a single type of 2'-substituted RNA-type nucleotide are more conveniently synthesized, the methods of the invention can be practiced with mixed duplex oligonucleotides having two or more types of RNA-type nucleotides. The function of an RNA segment may not be affected by an interruption caused by the introduction of a deoxynucleotide between two RNA-type trinucleotides, accordingly, the term RNA segment encompasses such as "interrupted RNA segment." An uninterrupted RNA segment is termed a contiguous RNA segment. In an alternative embodiment an RNA segment can contain alternating RNase-resistant and unsubstituted 2'-OH nucleotides. The mixed duplex oligonucleotides preferably have fewer than 100 nucleotides and more preferably fewer than 85 nucleotides, but more than 50 nucleotides. The first and second strands are Watson-Crick base paired. In one embodiment the strands of the mixed duplex oligonucleotide are covalently bonded by a linker, such as a single stranded hexa, penta or tetranucleotide so that the first and second strands are segments of a single oligonucleotide chain having a single 3' and a single 5' end. The 3' and 5' ends can be protected by the addition of a "hairpin cap" whereby the 3' and 5' terminal nucleotides are Watson-Crick paired to adjacent nucleotides. A second hairpin cap can, additionally, be placed at the junction between the first and second strands distant from the 3' and 5' ends, so that the Watson-Crick pairing between the first and second strands is stabilized.

The first and second strands contain two regions that are homologous with two fragments of the target gene, i.e., have the same sequence as the target gene. A homologous region contains the nucleotides of an RNA segment and may contain one or more DNA-type nucleotides of connecting DNA segment and may also contain DNA-type nucleotides that are not within the intervening DNA segment. The two regions of homology are separated by, and each is adjacent to, a region having a sequence that differs from the sequence of the target gene, termed a "heterologous region." The heterologous region can contain one, two or three mismatched nucleotides. The mismatched nucleotides can be contiguous or alternatively can be separated by one or two nucleotides that are homologous with the target gene. Alternatively, the heterologous region can also contain an insertion or one, two, three or of five or fewer nucleotides. Alternatively, the sequence of the mixed duplex oligonucleotide may differ from the sequence of the target gene only by the deletion of one, two, three, or five or fewer nucleotides from the mixed duplex oligonucleotide. The length and position of the heterologous region is, in this case, deemed to be the length of the deletion, even though no nucleotides of the mixed duplex oligonucleotide are within the heterologous region. The distance between the fragments of the target gene that are complementary to the two homologous regions is identically the length of the heterologous region when a substitution or substitutions is intended. When the heterologous region contains an insertion, the homologous regions are thereby separated in the mixed duplex oligonucleotide farther than their complementary homologous fragments are in the gene, and the converse is applicable when the heterologous region encodes a deletion.

The RNA segments of the mixed duplex oligonucleotides are each a part of a homologous region, i.e., a region that is identical in sequence to a fragment of the target gene, which segments together preferably contain at least 13 RNA-type nucleotides and preferably from 16 to 25 RNA-type nucleotides or yet more preferably 18-22 RNA-type nucleotides or most preferably 20 nucleotides. In one embodiment, RNA segments of the homology regions are separated by and adjacent to, i.e., "connected by" an intervening DNA segment. In one embodiment, each nucleotide of the heterologous region is a nucleotide of the intervening DNA segment. An intervening DNA segment that contains the heterologous region of a mixed duplex oligonucleotide is termed a "mutator segment."

In another embodiment of the present invention, the gene repair oligonucleobase is a single stranded oligodeoxynucleotide mutational vector (SSOMV), which is disclosed in International Patent Application PCT/US00/23457, U.S. Pat. Nos. 6,271,360, 6,479,292, and 7,060,500 which is incorporated by reference in its entirety. The sequence of the SSOMV is based on the same principles as the mutational vectors described in U.S. Pat. Nos. 5,756,325; 5,871,984; 5,760,012; 5,888,983; 5,795,972; 5,780,296; 5,945,339; 6,004,804; and 6,010,907 and in International Publication Nos. WO 98/49350; WO 99/07865; WO 99/58723; WO 99/58702; and WO 99/40789. The sequence of the SSOMV contains two regions that are homologous with the target sequence separated by a region that contains the desired genetic alteration termed the mutator region. The mutator region can have a sequence that is the same length as the sequence that separates the homologous regions in the target sequence, but having a different sequence. Such a mutator region can cause a substitution. Alternatively, the homologous regions in the SSOMV can be contiguous to each other, while the regions in the target gene having the same sequence are separated by one, two or more nucleotides. Such a SSOMV causes a deletion from the target gene of the nucleotides that are absent from the SSOMV. Lastly, the sequence of the target gene that is identical to the homologous regions may be adjacent in the target gene but separated by one two or more nucleotides in the sequence of the SSOMV. Such an SSOMV causes an insertion in the sequence of target gene.

The nucleotides of the SSOMV are deoxyribonucleotides that are linked by unmodified phosphodiester bonds except that the 3' terminal and/or 5' terminal internucleotide linkage or alternatively the two 3' terminal and/or 5' terminal internucleotide linkages can be a phosphorothioate or phosphoamidate. As used herein an internucleotide linkage is the linkage between nucleotides of the SSOMV and does not include the linkage between the 3' end nucleotide or 5' end nucleotide and a blocking substituent, see supra. In a specific embodiment the length of the SSOMV is between 21 and 55 deoxynucleotides and the lengths of the homology regions are, accordingly, a total length of at least 20 deoxynucleotides and at least two homology regions should each have lengths of at least 8 deoxynucleotides.

The SSOMV can be designed to be complementary to either the coding or the non-coding strand of the target gene. When the desired mutation is a substitution of a single base, it is preferred that both the mutator nucleotide be a pyrimidine. To the extent that is consistent with achieving the desired functional result it is preferred that both the mutator nucleotide and the targeted nucleotide in the complementary strand be pyrimidines. Particularly preferred are SSOMV that encode transversion mutations, i.e., a C or T mutator nucleotide is mismatched, respectively, with a C or T nucleotide in the complementary strand.

In addition to the oligodeoxynucleotide the SSOMV can contain a 5' blocking substituent that is attached to the 5' terminal carbons through a linker. The chemistry of the linker is not critical other than its length, which should preferably be at least 6 atoms long and that the linker should be flexible. A variety of non-toxic substituents such as biotin, cholesterol or other steroids or a non-intercalating cationic fluorescent dye can be used. Particularly preferred as reagents to make SSOMV are the reagents sold as Cy3™ and Cy5™ by Glen Research, Sterling Va., which are blocked phosphoroamidites that upon incorporation into an oligonucleotide yield 3,3,3', 3'-tetramethyl N,N'-isopropyl substituted indomonocarbocyanine and indodicarbocyanine dyes, respectively. Cy3 is the most preferred. When the indocarbocyanine is N-oxyalkyl substituted it can be conveniently linked to the 5' terminal of the oligodeoxynucleotide through as a phosphodiester with a 5' terminal phosphate. The chemistry of the dye linker between the dye and the oligodeoxynucleotide is not critical and is chosen for synthetic convenience. When the commercially available Cy3 phosphoramidite is used as directed the resulting 5' modification consists of a blocking substituent and linker together which are a N-hydroxypropyl, N'-phosphatidylpropyl 3,3,3',3'-tetramethyl indomonocarbocyanine.

In the preferred embodiment the indocarbocyanine dye is tetra substituted at the 3 and 3' positions of the indole rings. Without limitations as to theory these substitutions prevent the dye from being an intercalating dye. The identity of the substituents as these positions are not critical. The SSOMV can in addition have a 3' blocking substituent. Again the chemistry of the 3' blocking substituent is not critical.

Modified Enzymes

The genes encoding the enzymes involved in the fatty acid biosynthesis pathway are the preferred targets for mutation. In some embodiments the target gene encodes an acyl ACP thioesterase. In other embodiments the target gene encodes a keto acyl synthase (KAS). Mutations can be designed that reduce or eliminate the activity of an enzyme or that alter the activity of the enzyme (e.g., change the substrate selectivity). In some embodiments, the $\Delta^9$-stearoyl acyl-ACP desaturase gene is modified. In certain embodiments the FAD2 gene encoding $\Delta 12$ desaturase is targeted to decrease levels of linolenic acid (18:3) and linoleic acid (18:2) and increase levels of oleic acid (18:1).

In particular embodiments of the invention the native acyl ACP thioesterase is mutated. In one example, the acyl ACP thioesterase of *Brassica napus* is mutated in the region corresponding to amino acid residues 91-397 of SEQ ID NO:2. In preferred embodiments, one or more mutations are present at positions in a region corresponding amino acid residues 128-147 of SEQ ID NO:2, amino acid residues 175-206 of SEQ ID NO:2, amino acid residues 254-297 of SEQ ID NO:2, amino acid residues 333-335 of SEQ ID NO:2, or amino acid residues 365-397 of SEQ ID NO:2.

In other embodiments of the invention the native keto acyl synthase (KAS) enzyme is mutated. In one example, the KAS enzyme is a KAS II enzyme and is mutated in the region corresponding to amino acid residues 325-385 of SEQ ID NO:3. In preferred embodiments, one or more mutations are present at positions in a region corresponding amino acid residues 325-352 of SEQ ID NO:3 or amino acid residues 355-385 of SEQ ID NO:3. In more preferred embodiments, one or more mutations are in the region corresponding to amino acid residues 325-340 of SEQ ID NO:3, or even amino acid residues 331-337 of SEQ ID NO:3. In some embodiments, the amino acid corresponding to the conserved leucine residue at position 337 of SEQ ID NO:3 is mutated. In particular embodiments the amino acid corresponding to the conserved leucine residue at position 337 of SEQ ID NO:3 is mutated to phenylalanine, tyrosine, tryptophan or histidine. In other embodiments, the amino acid corresponding to the conserved phenylalanine residue at position 331 of SEQ ID NO:3 is mutated. In certain embodiments, the amino acid corresponding to the conserved phenylalanine residue at position 331 of SEQ ID NO:3 is mutated to glycine, alanine, serine, threonine, cysteine, or valine.

Delivery of Gene Repair Oligonucleobases into Plant Cells

Any commonly known method can be used in the methods of the present invention to transform a plant cell with a gene repair oligonucleobases. Exemplary methods include the use of microcarriers or microfibers, electroporation, and microinjection and are described below.

In some embodiments, metallic microcarriers (microspheres) are used to introduce large fragments of DNA into plant cells having cellulose cell walls by projectile penetration (biolistic delivery) and is well known to those skilled in the relevant art. General techniques for selecting microcarriers and devices for projecting them are described in U.S. Pat. Nos. 4,945,050; 5,100,792 and 5,204,253.

Specific conditions for using microcarriers in the methods of the present invention are described in International Publication WO 99/07865, U.S. Ser. No. 09/129,298. For example, ice cold microcarriers (60 mg/mL), mixed duplex oligonucleotide (60 mg/mL), 2.5 M $CaCl_2$ and 0.1 M spermidine are added in that order; the mixture gently agitated, e.g., by vortexing, for 10 minutes and let stand at room temperature for 10 minutes, whereupon the microcarriers are diluted in 5 volumes of ethanol, centrifuged and resuspended in 100% ethanol. Exemplary concentrations of the components in the adhering solution include 8-10 µg/µL microcarriers, 14-17 µg/µL mixed duplex oligonucleotide, 1.1-1.4 M $CaCl_2$ and 18-22 mM spermidine. In one example, the component concentrations are 8 µg/µL microcarriers, 16.5 µg/µL mixed duplex oligonucleotide, 1.3 M $CaCl_2$ and 21 mM spermidine.

Gene repair oligonucleobases can also be introduced into plant cells for the practice of the present invention using microfibers to penetrate the cell wall and cell membrane. U.S. Pat. No. 5,302,523 to Coffee et al. describes the use of 30×0.5 µm and 10×0.3 µm silicon carbide fibers to facilitate transformation of suspension maize cultures of Black Mexican Sweet. Any mechanical technique that can be used to introduce DNA for transformation of a plant cell using microfibers can be used to deliver gene repair oligonucleobases.

One example of microfiber delivery of a gene repair oligonucleobase is as follows. Sterile microfibers (2 µg) are suspended in 150 µL of plant culture medium containing about 10 µg of a mixed duplex oligonucleotide. A suspension culture is allowed to settle and equal volumes of packed cells and the sterile fiber/nucleotide suspension are vortexed for 10 minutes and plated. Selective media are applied immediately or with a delay of up to about 120 hours as is appropriate for the particular trait.

In an alternative embodiment, the gene repair oligonucleobases can be delivered to the plant cell by electroporation of a protoplast derived from a plant part. The protoplasts are formed by enzymatic treatment of a plant part, particularly a leaf, according to techniques well known to those skilled in the art. (See, e.g., Gallois et al., 1996, in Methods in Molecular Biology 55:89-107, Humana Press, Totowa, N.J.; Kipp et al., 1999, in Methods in Molecular Biology 133:213-221, Humana Press, Totowa, N.J.) The protoplasts need not be cultured in growth media prior to electroporation. Illustrative conditions for electroporation are $3 \times 10^5$ protoplasts in a total volume of 0.3 mL with a concentration of gene repair oligonucleobase of between 0.6-4 µg/mL.

In yet another alternative embodiment, the gene repair oligonucleobase can be delivered to the plant cell by whiskers or microinjection of the plant cell. The so-called whiskers technique is performed essentially as described in Frame et al., 1994, Plant J. 6:941-948. The gene repair oligonucleobase is added to the whiskers and used to transform the plant cells. The gene repair oligonucleobase may be co-incubated with plasmids comprising sequences encoding proteins capable of forming recombinase and/or gene repair complexes in plant cells such that gene repair is catalyzed between the oligonucleotide and the target sequence in the target gene.

Selection of Plants Having the Modified Enzyme

Plants or plant cells expressing the modified enzyme can be identified through any of a number of means. In one method, a co-conversion strategy using gene repair oligonucleobases (RONs) to target both a selectable conversion (i.e., a marker) and a non-selectable conversion (e.g., a target gene of interest) in the same experiment. For example, the ALS (or AHAS) gene in canola can be modified by single amino acid changes to provide resistance (through gene conversion) to the imidazolinones (IMI) class of herbicides in vitro. The simultaneous delivery of gene repair oligonucleobases targeting conversion of the ALS gene and the other target gene(s)/allele(s) and selecting the resulting regenerating calli on IMI, identifies the conversion competent population. In this way, the cells to which RONs were not delivered or were unable to transmit the conversions specified by the RON would be eliminated. Since delivery of RONs targeting unrelated genes is not expected to be selective, at some frequency, regenerating calli having an ALS conversion would also be expected to have a conversion in one of the other targeted genes. Conversion events would be resolved by single nucleotide polymorphism (SNP) analysis.

Thus, genomic DNA is extracted from leaf material from individual plants regenerated from protoplasts deemed conversion competent and screening of the individual DNA samples using a SNP detection technology, e.g. allele-specific Polymerase Chain Reaction (ASPCR), for each target. Putative positive plants for each target may be hardened and transferred to soil. To independently confirm the sequence change in positive plants, the appropriate region of the target gene may be PCR amplified and the resulting amplicon either sequenced directly or cloned and multiple inserts sequenced. Where multiple changes will be made in the same gene, the convertant can be backcrossed to its parent enabling the segregation of converted ALS resistance gene from the target gene.

Alternatively, the incorporation of the mutation into the gene of interest can be identified by any of a number of molecular biology techniques designed to detect single nucleotide mutations in extracted nucleic acid (e.g., amplification methods such as PCR and single nucleotide primer extension analysis). Larger mutations can be detected by amplification and sequencing of the region of the target gene to be mutated.

Alternatively, plants or plant cells containing the modified enzyme can be identified by, for example, analysis of the composition of fatty acids produced by the plant. Thus, the plant can be grown and oils extracted and analyzed using methods known in the art (e.g., gas chromatography).

Production of a Transgenic Plant Expressing Two Thioesterase Transgenes

Transgenic plants expressing two transgenes encoding thioesterases having preference for acyl substrates of differing lengths of medium chain fatty acids may be generated by methods well-known in the art.

Thus, plant thioesterases can be obtained from a variety of sources. Plants producing significant quantities of medium-chain fatty acids are the preferred sources of DNA sequences encoding medium-chain preferring plant thioesterases. For example, several species in the genus *Cuphea* accumulate triglycerides containing medium-chain fatty acids in their seeds, e.g., procumbens, lutea, hookeriana, hyssopifolia, wrightii and inflata. In addition, elm (*Ulmus americana*) has been shown to contain significant medium chain fatty acids. Further, members of the Lauraceae family: e.g., Pisa (*Actinodophne hookeri*), Sweet Bay (*Laurus nobilis*), and California Bay (*Umbellularia californica*) produce seeds having medium chain fatty acids. Additional sources include, Myristicaceae, Simarubaceae, Vochysiaceae, and Salvadoraceae, and rainforest species of *Erisma, Picramnia* and *Virola*, which have been reported to accumulate C14 fatty acids.

Some examples of plants harboring medium chain-preferring thioesterases and their preferred substrate are shown in Table 1.

TABLE 1

Thioesterases and the substrates thereof

| Chain length of thioesterase substrate | Exemplary sources of thioesterase |
|---|---|
| C8 | *Cuphea hookeriana, Cuphea palustris* |
| C10 | *Cuphea hookeriana, Ulmus americana* |
| C12 | *Umbellularia californica* |

Other plants may also be sources of desirable thioesterases which have preferences for particular fatty acyl chain lengths. Such additional plant thioesterases may be identified by analyzing the triacylglyceride composition of various plant oils. The presence of a specific thioesterase may be confirmed by assays using the appropriate acyl-ACP substrate. For example, an assay a for C10-preferring acyl-ACP thioesterase, is described in WO 91/16421 and may be used for such an analysis.

Plant expression constructs containing a DNA sequence encoding a plant thioesterase of interest may be used in a wide variety of plants, in particular, plants employed in the production of vegetable oils for edible and industrial uses. Preferred plants are oilseed crops including, but are not limited to, rapeseed (canola and high erucic acid varieties), sunflower, safflower, cotton, *Cuphea*, soybean, peanut, coconut and oil palms, and corn.

Expression constructs, for which the host cell is a plant cell, will include regulatory regions (e.g., promoters and termination regions) that are functional in plants. Thus, the open reading frame (ORF) encoding the protein to be expressed in the resulting transgenic plant is joined at its 5' end to a transcription initiation regulatory region or promoter, such as the promoter found in the native gene. Numerous other transcription initiation regions are available which provide for a wide variety of constitutive or inducible transcription of the structural gene functions. Among transcriptional initiation regions used for plants are such regions associated with the structural genes such as for CaMV 35S and nopaline and mannopine synthases, or with napin, ACP promoters and the like. The transcription/translation initiation regions corresponding to such structural genes are found immediately 5' upstream to the respective start codons. If a particular promoter is desired, such as a promoter native to the plant host of interest or a modified promoter, i.e., having transcription initiation regions derived from one gene source and translation initiation regions derived from a different gene source, including the sequence encoding the plant thioesterase of interest, or enhanced promoters, such as double 35S CaMV promoters, the sequences may be joined together using standard techniques. For most applications desiring the expression of medium-chain thioesterases in plants, the use of seed specific promoters are preferred. Further, depending on the method for introducing the recombinant constructs into the host cell, further components in the expression construct may be required. For example, DNA encoding a selection marker for transformant cells may be included in the expression construct. Thus, the construct may provide for resistance to a cytotoxic agent (e.g. antibiotic, heavy metal, toxin, etc.), complementation providing prototrophy to an auxotrophic host, viral immunity or the like. Depending upon the number of different host species the expression construct or components thereof are introduced, one or more markers may be employed, where different conditions for selection are used for the different hosts.

Various methods of plant transformation are well-known in the art. For example transformation via *Agrobacterium* infection, microinjection, DNA particle bombardment, and electroporation are commonly used. Furthermore, as newer methods are available to transform crops, such methods may also be used. Examples of the transformation of plants can be found in U.S. Pat. No. 5,667,997.

In order to express more than one transgene, an expression construct may be generated for each transgene. Plants can then transformed with a first expression construct comprising a first transgene and plant selectable marker. Regenerants grown on selection media may be screened for expression of the transgene using e.g. Western blotting techniques. Plants expressing transgene are grown to maturity and allowed to set seed from which a second generation of plant can be generated (T2).

The T2 generation is used for a second round of transformation, now with a second expression construct comprising a second transgene and a second plant selectable marker. (Methods to remove or inactivate plant selectable markers are known in the art (e.g. as disclosed in WO92/01370). Regenerants are grown on selective media to maturity and allowed to set seed from which the next generation of plants are grown (T3). The T3 generation is screened for an increase in medium chain fatty acids as compared to the wild type plant.

Generation of Genetically Modified Plants Having Oil with a Desirable Balance of Medium Chain Fatty Acids and Monounsaturated Fatty Acids.

In some embodiments decreased levels of linolenic acid (18:3) and linoleic acid (18:2) as well as increased levels of oleic acid (18:1) are achieved in a genetically modified plant by reducing the expression or activity of the Δ12 desaturase (FAD2 gene); preferably the targeted FAD2 gene is a rapeseed, cotton, flax, peanut, palm, safflower, soybean, sunflower, *Cuphea*, or corn FAD2 gene. In preferred embodiments, the expression or activity of FAD2 is reduced by creating a stop codon in the coding sequence of the gene; or by deleting or adding a nucleotide to create a frameshift mutation.

In certain preferred embodiments, the $\Delta^9$-stearoyl acyl-ACP desaturase gene is modified in a genetically modified plant to increase the levels of palmitoleic acid (C16:1) and/or oleic acid (18:1); preferably the genetically modified plant is selected from the group consisting of rapeseed, cotton, flax, peanut, palm, safflower, soybean, sunflower, *Cuphea*, and corn. In certain preferred embodiments the expression and or activity of $\Delta^9$-stearoyl acyl-ACP desaturase is increased to facilitate an increase in the production of monounsaturated fatty acids and a decrease in saturated fatty acids; more preferably the levels of C16:1 and/or C18:1 are increased and the levels of C16:0 and/or C18:0 are decreased in the genetically altered plant as compared to a native plant. In other embodiments the of $\Delta^9$-stearoyl acyl-ACP desaturase gene is modified such that the genetically modified plant produces increased levels of C16:1. In certain embodiments the of $\Delta^9$-stearoyl acyl-ACP desaturase gene is modified such that it exhibits increased activity with palmitoyl-ACP. See, for example, Cahoon, E. B. and Shanklin, J, 2000. Substrate-dependent mutant complementation to select fatty acid desaturase variants for metabolic engineering of plant seed oil. Proc. Nat. Acad. Sci. 97(22): 12350-12355. In related embodiments the increased production of C16:0 is achieved by transformation of rapeseed with the $\Delta^9$-stearoyl acyl-ACP gene from *macadamia* (*Macadamia integrifolia*), sea buckthorn (Hippophae rhamnoides) or cat's claw (Doxantha unguis-cati). In certain embodiments, the activity or expression of the KASII gene is reduced using methods as disclosed herein in addition to the modification of the $\Delta^9$-stearoyl acyl-ACP gene to achieve even higher levels of 18:1 and 16:1 fatty acids; in more preferred embodiments the PTE enzymes of the genetically modified plant are also modified as disclosed herein to produce increased levels of short chain fatty acids; in more preferred embodiments the $\Delta 12$ desaturase of the genetically modified plant is also modified to have decreased activity or expression.

In certain preferred embodiments a plant; preferably a rapeseed, cotton, flax, peanut, palm, safflower, soybean, sunflower, or corn plant; is genetically modified to have increased levels of short/medium chain fatty acids as disclosed herein by (1) altering the substrate specificity of the palmitoyl thioesterase (PTE) to increase activity with capryloyl-ACP (C8), caproyl-ACP (C10), and lauroyl-ACP (C12) or by transforming with acyl-ACP thioesterase genes having short chain length specificity from *Cuphea*, coconut, palm, Babassu, tucum (*Astrocaryum vulgare*), elm (*Ulmus Americana*), Japanese *Zelkova* (*Zelkova serrata*) or California bay (*Umbellularia californica*); and (2) decreasing the activity of the KAS II gene. In certain preferred embodiments a plant is genetically modified to have increased levels of short/medium chain fatty acids by altering the PTE and/or KASII genes as disclosed herein; and is further modified to have decreased levels of polyunsaturated fatty acids (preferably decreased levels of C18:2 and C18:3) by reducing the expression or activity of $\Delta 12$ desaturase; more preferably the plant is further modified by modifying the $\Delta^9$-stearoyl acyl-ACP desaturase gene to increase the levels of palmitoleic acid (C16:1) and/or oleic acid (18:1) and have decreased levels of levels of C16:0 and/or C18:0.

Calculation of Predicted Melting Point of Fatty Acid Methyl Esters.

The predicted melting point, $P_{Tm}$, of a blend of fatty acid methyl esters may be computed using the amount of each fatty acid methyl ester, expressed as weight/100 g blend, and the following equation.

$$P_{Tm} = [A(-71.0)(10.0) + B(-40.0)(4.5) + C(-18.0)(1.2) + D(5.2)(1.0) + E(19.0)(0.60) + F(30.7)(1.35) + G(37.8)(2.15) + H(-19.9)(1.10) + I(-35.0)(0.65) + J(-57)(0.2) + K(54.5)(10.0) + L(53.0)(2.0) + M(57.4)(2.0)]*(0.01),$$

A is the percent (w/w) caproic ME (6:0) in the blend;
B is the percent (w/w) caprylic ME (8:0) in the blend;
C is the percent (w/w) capric ME (10:0) in the blend;
D is the percent (w/w) lauric ME (12:0) in the blend;
E is the percent (w/w) myristic ME (14:0) in the blend;
F is the percent (w/w) palmitic ME (16:0) in the blend;
G is the percent (w/w) stearic ME (18:0) in the blend;
H is the percent (w/w) oleic ME (18:1) in the blend;
I is the percent (w/w) linoleic ME (18:2) in the blend;
J is the percent (w/w) linolenic ME (18:3) in the blend;
K is the percent (w/w) arachidic ME (20:0) in the blend;
L is the percent (w/w) behenic ME (22:0) in the blend; and
M is the percent (w/w) lignoceric ME (24:0) in the blend.

In some embodiments, the predicted melting point may be used to identify blends that are suitable for use as a biodiesel. In these embodiments, the predicted melting point is compared to a cut-off value (i.e., a desired melting point for a biodiesel). Those blends having a predicted melting point less than or equal to the cut-off value are suitable for use as a biodiesel.

The following examples serve to illustrate the present invention. These examples are in no way intended to limit the scope of the invention.

Example 1

Fatty Acid Methyl Ester Blend 1

A blend of fatty acid methyl esters ("Blend 1") having the composition of fatty acid methyl esters as set forth in the table below, is prepared by mixing together the fatty acid methyl esters using the volumes presented in the below table to make 100 g of Blend 1.

| Component | Blend 1 | mL/100 g |
|---|---|---|
| caproic ME (6:0) | 1% | 1.1 |
| caprylic ME (8:0) | 20 | 22.8 |
| capric ME (10:0) | 30 | 34.4 |
| lauric ME (12:0) | 20 | 23.0 |
| myristic ME (14:0) | 4 | 4.7 |
| palmitic ME (16:0) | 2 | 2.3 |
| stearic ME (18:0) | 2 | 2.1 |
| oleic ME (18:1) | 15 | 17.1 |
| linoleic ME (18:2) | 1 | 1.1 |
| linolenic ME (18:3) | 1 | 1.1 |
| arachidic ME (20:0) | 1 | 1.2 |
| behenic ME (22:0) | 1 | 1.2 |
| lignoceric ME (24:0) | 1 | 1.2 |

The predicted melting point of Blend 1, $P_{Tm}$, as computed by invention methods, is −41.6° C.

Example 2

Fatty Acid Methyl Ester Blend 2

A blend of fatty acid methyl esters ("Blend 2") having the composition of fatty acid methyl esters as set forth in the table below, is prepared by mixing together the fatty acid methyl esters using the volumes presented in the above table to make 100 g of Blend 2.

| Component | Blend 2 | mL/100 g |
|---|---|---|
| caproic ME (6:0) | 1% | 1.1 |
| caprylic ME (8:0) | 10 | 11.4 |
| capric ME (10:0) | 35 | 40.1 |
| lauric ME (12:0) | 25 | 28.7 |
| myristic ME (14:0) | 5 | 5.8 |
| palmitic ME (16:0) | 2 | 2.3 |
| stearic ME (18:0) | 2 | 2.1 |
| oleic ME (18:1) | 15 | 17.1 |
| linoleic ME (18:2) | 1 | 1.1 |
| linolenic ME (18:3) | 1 | 1.1 |
| arachidic ME (20:0) | 1 | 1.2 |
| behenic ME (22:0) | 1 | 1.2 |
| lignoceric ME (24:0) | 1 | 1.2 |

The predicted melting point of Blend 2, $P_{Tm}$, as computed by invention methods, is −24.3° C.

Example 3

Fatty Acid Methyl Ester Blend 3

A blend of fatty acid methyl esters ("Blend 3") having the composition of fatty acid methyl esters as set forth in the table below, is prepared by mixing together the fatty acid methyl esters using the volumes presented in the above table to make 100 g of Blend 3.

| Component | Blend 3 | ml/100 g |
|---|---|---|
| caproic ME (6:0) | 1 | 1.1 |
| caprylic ME (8:0) | 5 | 5.7 |
| capric ME (10:0) | 35 | 40.1 |
| lauric ME (12:0) | 30 | 34.5 |
| myristic ME (14:0) | 5 | 5.8 |
| palmitic ME (16:0) | 2 | 2.3 |
| stearic ME (18:0) | 2 | 2.1 |
| oleic ME (18:1) | 15 | 17.1 |
| linoleic ME (18:2) | 1 | 1.1 |
| linolenic ME (18:3) | 1 | 1.1 |
| arachidic ME (20:0) | 1 | 1.2 |
| behenic ME (22:0) | 1 | 1.2 |
| lignoceric ME (24:0) | 1 | 1.2 |

The predicted melting point of Blend 3, $P_{Tm}$, as computed by invention methods, is $-15.0°$ C.

Example 4

Fatty Acid Methyl Ester Blend 4

A blend of fatty acid methyl esters ("Blend 4") having the composition of fatty acid methyl esters as set forth in the table below, is prepared by mixing together the fatty acid methyl esters using the volumes presented in the above table to make 100 g of Blend 4.

| Component | Blend 4 | mL/100 g |
|---|---|---|
| caproic ME (6:0) | 1% | 1.1 |
| caprylic ME (8:0) | 5 | 5.7 |
| capric ME (10:0) | 30 | 34.4 |
| lauric ME (12:0) | 30 | 34.5 |
| myristic ME (14:0) | 5 | 5.8 |
| palmitic ME (16:0) | 7 | 8.2 |
| stearic ME (18:0) | 2 | 2.1 |
| oleic ME (18:1) | 15 | 17.1 |
| linoleic ME (18:2) | 1 | 1.1 |
| linolenic ME (18:3) | 1 | 1.1 |
| arachidic ME (20:0) | 1 | 1.2 |
| behenic ME (22:0) | 1 | 1.2 |
| lignoceric ME (24:0) | 1 | 1.2 |

The predicted melting point of Blend 4, $P_{Tm}$, as computed by invention methods, is $-11.9°$ C.

Example 5

Oil Blend A

A blend of two oils ("Blend 4") having the fatty acid composition set forth below is prepared by mixing together coconut oil and *Cuphea lanceolata* oil having the fatty acid composition set forth below.

| Component | Blend A | *Cuphea lancelolata* oil | Coconut oil |
|---|---|---|---|
| caproic acid (6:0) | 0.4% | 0 | 0.5 |
| caprylic acid (8:0) | 5.5 | 0.6 | 7.1 |
| capric acid (10:0) | 25 | 83.2 | 6 |
| lauric acid (12:0) | 36 | 2.1 | 47.1 |
| myristic acid (14:0) | 14 | 2 | 18.5 |
| palmitic acid (16:0) | 7.7 | 3.4 | 9.1 |
| stearic acid (18:0) | 2.1 | 0 | 2.8 |
| oleic acid (18:1) | 6.0 | 3.4 | 6.8 |
| linoleic acid (18:2) | 2.6 | 4.6 | 1.9 |
| linolenic acid (18:3) | 0.1 | | 0.1 |
| arachidic acid (20:0) | 0.1 | | 0.1 |
| behenic acid (22:0) | 0 | 0 | 0 |
| lignoceric ME (24:0) | 0 | 0 | 0 |

Blend A can be prepared by mixing 75% by weight of the above coconut oil with 25% by weight of the above *Cuphea lanceolata* oil. 25 gms of *Cuphea lanceolata* oil (25 gm/0.92 gm/ml=27.2 mL) is combined with 75 gms of soybean oil (75 gm/0.924 gm/mL=81.2 mL) to make 100 gm Blend A.

Example 6

Conversion of Oils to FAMES

Various types of commercial vegetable oil (including soy, canola, corn, *macadamia*, olive, safflower, sunflower, peanut, walnut, palm, coconut, and castor oil) were obtained from retail sources. 200 gm of each oil was weighed into a glass screw cap bottle and combined with 2 volumes (w/v) of sodium methoxide reagent (5% w/v sodium methoxide/methanol). After mixing for 2 hours at room temperature, 50 ml hexane was added, mixed vigorously and the phases were allowed to separate. The lower glycerol-containing layer was removed and discarded. The upper layer was treated under vacuum in a rotary evaporator to remove hexane and any remaining volatiles. The final solution of FAME was stored under nitrogen gas at room temperature in a tightly capped glass bottle.

Example 7

Conversion of Fatty Acids to FAMES 100 grams of various fatty acids, or mixtures of fatty acids, were weighed into a glass bottle and combined with 200 ml of anhydrous methanol/1% sulfuric acid. Each mixture was covered with nitrogen gas and the container tightly capped. The reaction bottle was placed in an incubator oven for 4 hr. at 50° C. During the incubation, the mixture was shaken occasionally to mix the reactants. The mixture was transferred to a glass reparatory funnel, and combined with 100 ml of 5% (w/v) sodium chloride aqueous solution. The mixture was shaken vigorously and the phases allowed to separate by standing. The lower aqueous layer was removed and discarded. The upper layer was transferred to a clean, dry bottle and combined with 5 gm of anhydrous sodium sulfate. This mixture was vigorously shaken until all visible water droplets were removed. The mixture was then filtered thru Whatman 1 filter paper. The sodium sulfate and filter apparatus was rinsed in hexane to recover additional FAME and the wash added to the non-aqueous fraction. The combined filtrate and washes were placed into a rotary evaporator under vacuum to remove hexane and remaining volatiles. The final solution of FAME was transferred to a brown glass bottle, covered with nitrogen gas, tightly capped with a Teflon lined cap, and stored at 4° C. Other esters were synthesized using this protocol substituting ethanol, n-propanol, iso-propanol, n-butanol, sec-butanol, or t-butanol in place of the methanol used above.

Example 8

Cold Temperature Testing of Alkyl Ester Mixtures

Cold temperature properties of alkyl esters and ester mixtures were tested by pipetting aliquots of pure alkyl esters or ester mixtures obtained from oils or fatty acids as described above, into 10 mm×100 mm glass test tubes, to a final volume of 1.0 ml. The tubes were capped with polypropylene snap caps and placed in plastic racks. The racked tubes were then immersed to a depth of 1-2 cm above the top of the sample, in a chilled solution of 50% ethylene glycol/water. A series of water baths were used to sequentially test samples at 0, –10, –15, –20, and –25° C. Samples were held at the test temperature for 1 hr and each tube was withdrawn and examined for the presence of cloudiness, solidification, and pour/flow characteristics. In addition, select samples were sent to an independent testing laboratory (Intertek-Caleb-Brett Laboratories) and evaluated for pour point, cloud point, and cold filter plugging using the appropriate ASTM standard methods for diesel fuel (ASTM D-97-06, ASTM D-2500-05, and ASTM D6371). Cloud points of esters and ester mixtures were also determined using a portable diesel fuel cloud point analyzer, model CPA-T30 (Phase Technology Corp.). A 10 ml plastic syringe was filled with ester or ester mixture and injected into the instrument. After 10 minutes the instrument provided a precise cloud point temperature readout.

Example 9

Melting Points of B100 Seed Oils and #2 Diesel

A series of B100 biodiesel fluids (fatty acid alkyl esters) were made from vegetable oils including soy, canola, corn, *macadamia*, olive, safflower, sunflower, peanut, walnut, palm, coconut, and castor oils in accordance with the procedures described in Example 6. These fuels were compared with a commercially obtained petroleum-based diesel #2 (Shell Oil Co., San Diego, Calif.) for cold flow properties in accordance with the procedures described in Example 8. The effects of incubating each fluid at various temperatures between +20 and –20° C. are shown in the table below, which shows whether the fluid was liquid or solid after incubating at a given temperature for 1 hr (pour point). Diesel fuel remained liquid to –15° C. but was solid after 1 hr. at –20° C. In contrast, the vegetable oil based fatty acid methyl esters solidified at much lower temperatures. Palm oil methyl ester was solid at +5° C. The best performing vegetable oil based esters were canola and castor which were both solid at –15° C. Thus, none of the vegetable oil methyl esters had cold temperature properties that equal diesel fuel or the target of a cloud point of less than –20° C.

| Base Oil | % | RT | 0° C. | –10° C. | –15° C. | –20° C. |
|---|---|---|---|---|---|---|
| SOY | 100 | L | L | S | S | S |
| CANOLA | 100 | L | L | L | CL | S |
| CORN | 100 | L | L | S | S | S |
| MACADAMIA | 100 | L | S | S | S | S |
| OLIVE | 100 | L | L | S | S | S |
| SAFFLOWER | 100 | L | L | S | S | S |
| SUNFLOWER | 100 | L | CL | S | S | S |
| PEANUT | 100 | L | S | S | S | S |
| WALNUT | 100 | L | L | S | S | S |
| PALM | 100 | L | S | S | S | S |
| COCONUT | 100 | L | L | S | S | S |
| CASTOR | 100 | L | L | L | S | S |
| DIESEL #2 | 100 | L | L | L | L | L |

Key:
L = liquid
S = solid
CL = cloudy liquid
RT = Room Temperature

Example 10

C8 and C10 FAMES Lower the Melting Point of Soy and Canola B100

The cold temperature properties of vegetable oil derived methyl esters were improved by the addition of short chain fatty acid methyl esters. Soy oil methyl ester was solid at –10° C. When 30% (v/v) C8 methyl ester (methyl octanoate) was added to soy oil methyl ester, the mixture remained liquid at –10° C. When the C8 methyl ester was increased to 60% (v/v) the mixture remained liquid to –20° C. Addition of C10 methyl ester (methyl decanoate) had an identical effect on the pour point of soy derived methyl ester. Cold temperature performance of canola oil derived methyl ester was also improved by the addition of short chain methyl esters. Addition of 40% C8 methyl ester to canola methyl ester lowered the observed pour point to –20° C. Addition of C10 methyl ester to canola had a similar effect on observed pour points. Addition of a mixture of C8/C10 esters to canola or soy methyl esters also depressed the pour point of the mixture.

| Base Oil | % | C8ME | C10ME | RT | 0° C. | –10° C. | –15° C. | –20° C. |
|---|---|---|---|---|---|---|---|---|
| Soy | 100 | | 0 | L | L | S | S | S |
| Soy | 90 | | 10 | L | L | S | S | S |
| Soy | 80 | | 20 | L | L | S | S | S |
| Soy | 70 | | 30 | L | L | S | S | S |
| Soy | 60 | | 40 | L | L | L | S | S |
| Soy | 50 | | 50 | L | L | L | S | S |
| Soy | 100 | 0 | | L | L | S | S | S |
| Soy | 90 | 10 | | L | L | S | S | S |
| Soy | 80 | 20 | | L | L | S | S | S |
| Soy | 70 | 30 | | L | L | L | S | S |

| Base Oil | % | C8ME | C10ME | RT | 0° C. | -10° C. | -15° C. | -20° C. |
|---|---|---|---|---|---|---|---|---|
| Soy | 60 | 40 | | L | L | L | S | S |
| Soy | 50 | 50 | | L | L | L | S | S |
| Soy | 40 | 60 | | L | L | L | L | L |
| Soy | 30 | 70 | | L | L | L | L | L |
| Soy | 20 | 80 | | L | L | L | L | L |
| Soy | 10 | 90 | | L | L | L | L | L |
| Canola | 100 | 0 | | L | L | CL | S | S |
| Canola | 90 | 10 | | L | L | CL | S | S |
| Canola | 80 | 20 | | L | L | CL | CL | S |
| Canola | 70 | 30 | | L | L | L | CL | S |
| Canola | 60 | 40 | | L | L | L | CL | CL |
| Canola | 50 | 50 | | L | L | L | CL | CL |
| Canola | 40 | 60 | | L | L | L | L | CL |
| Canola | 30 | 70 | | L | L | L | L | L |
| Canola | 20 | 80 | | L | L | L | L | L |
| Canola | 10 | 90 | | L | L | L | L | L |
| Canola | 0 | 100 | | L | L | L | L | L |
| Canola | 100 | | 0 | L | L | CL | S | S |
| Canola | 90 | | 10 | L | L | CL | S | S |
| Canola | 80 | | 20 | L | L | CL | CL/S | S |
| Canola | 70 | | 30 | L | L | L | CL | CL |
| Canola | 60 | | 40 | L | L | L | CL | CL |
| Canola | 50 | | 50 | L | L | L | CL | CL |

Key:
L = liquid
S = solid
CL = cloudy liquid
RT = Room Temperature
C8ME = methyl octanoate
C10ME = methyl decanoate

Example 11

Melting Properties of Various Whole Oil B2-B100 Biodiesel Blends

Mixtures of diesel fuel with vegetable oil-derived methyl esters were also tested for cold temperature properties. Diesel fuel was tested with 2% (B2), 5% (B5), 20% (B20) (v/v) vegetable oil derived methyl ester, along with pure vegetable oil derived methyl ester (B100). Addition of vegetable oil-derived methyl ester to diesel fuel had no observable effect on pour points of the mixtures except with the B20 blends. Canola, castor and soy had no effect on the B20 pour point, while corn, olive, safflower, sunflower, peanut, palm, and coconut all raised the observed pour points of the B20 blends compared to pure diesel fuel.

| Base Oil | RT | 0° C. | -10° C. | -15° C. | -20° C. |
|---|---|---|---|---|---|
| Soy B2 | L | L | L | L | S |
| B5 | L | L | L | L | S |
| B20 | L | L | L | S | S |
| B100 | L | L | S | S | S |
| CANOLA B2 | L | L | L | L | S |
| B5 | L | L | L | L | S |
| B20 | L | L | L | L | S |
| B100 | L | L | S | S | S |
| CORN B2 | L | L | L | L | S |
| B5 | L | L | L | L | S |
| B20 | L | L | L | S | S |
| B100 | L | L | S | S | S |
| OLIVE B2 | L | L | L | L | S |
| B5 | L | L | L | L | S |
| B20 | L | L | L | S | S |
| B100 | L | L | S | S | S |
| SAFFLOWER B2 | L | L | L | L | S |
| B5 | L | L | L | L | S |
| B20 | L | L | L | L | S |
| B100 | L | L | S | S | S |
| SUNFLOWER B2 | L | L | L | L | S |
| B5 | L | L | L | L | S |
| B20 | L | L | L | S | S |
| B100 | L | L | S | S | S |
| PEANUT B2 | L | L | L | L | S |
| B5 | L | L | L | L | S |
| B20 | L | L | L | S | S |
| B100 | L | S | S | S | S |
| PALM B2 | L | L | L | L | S |
| B5 | L | L | L | L | S |
| B20 | L | L | L | L | S |
| B100 | L | S | S | S | S |
| COCONUT B2 | L | L | L | L | S |
| B5 | L | L | L | L | S |
| B20 | L | L | L | L | S |
| B100 | L | L | S | S | S |
| CASTER B2 | L | L | L | L | S |
| B5 | L | L | L | L | S |
| B20 | L | L | L | L | S |
| B100 | L | L | S | S | S |

Key:
B2 = 2% methyl ester + 98% Diesel #2
B5 = 5% methyl ester + 95% Diesel #2
B20 = 20% methyl ester + 80% Diesel #2
B100 = 100% methyl ester
L = liquid
S = solid

Example 12

Effects of Long Chain Saturates on Melting Point

Fatty acid methyl esters were tested for cold temperature performance as detailed above. The chart below shows the effect of adding long chain saturated fatty acids to C18:1 methyl ester (methyl octadecenoate). Pure C18:1 methyl ester is liquid at -20° C. but addition of C18:0 methyl octadecanoate) raises the observed pour point to as high as +5° C. with as little as 2% C18:0 present in the mixture; at 1% C18:0 the pour point of the mixture is 0° C. Similarly, C16 mixtures with C18:1 dramatically raises the pour point. A mixture of 9% (v/v) C16 methyl ester (methyl hexadecanoate) with 91% C18:1 was solid at −5° C. As little as 3% C16:0 resulted in a solid at −15° C. C14:0 methyl ester (methyl tetradecanoate) at concentrations as low as 1% resulted in a solid at −20° C., and 30% C14:0 was solid at −10° C. Mixtures with C12:0 (methyl dodecanoate) presented an interesting and unexpected result. At levels of C12 between 1% and 5% the mixtures were solid at −20° C., but between 6% and 20% C12 mixtures with C18:1 remained liquid at −20° C. Accordingly, the presence of C12:0 in a biodiesel at 6-20%; or more preferably at 6-10%, has surprising beneficial effects on cold flow properties. Thus, while the longer chain saturated FAMEs significantly raised the pour point of mixtures with C18:1, C14 had a much smaller effect and C12 had almost no effect at concentrations up to 20% (v/v).

Example 13

Genetically Modified Rapeseed Plant

A rapeseed plant is genetically modified to produce an oil with a desirable balance of medium chain fatty acids and monounsaturated fatty acids as discussed herein, namely the rapeseed plant is genetically modified to have relatively increased levels of short/medium chain fatty acids; relatively increased levels of monounsaturated C16:0 and C18:0 fatty acids; and relatively decreased levels of polyunsaturated C18:2 and C18:3 fatty acids. The following genetic modifications are performed: (1) The activity of Δ12 desaturase is reduced by using gene repair oligonucleotide bases to introduce a stop codon in the coding sequence of the FAD2 gene to decrease the level of linolenic acid (18:3) and linoleic acid (18:2) as well as increase the level of oleic acid (18:1); (2) the activity of the $\Delta^9$-stearoyl acyl-ACP desaturase gene is modified by transforming the rapeseed plant with the $\Delta^9$-stearoyl acyl-ACP gene from *macadamia* (*Macadamia integrifolia*),

| C12ME | C14ME | C16ME | C18ME | C18:1ME | RT | 0° C. | −10° C. | −15° C. | −20° C. |
|---|---|---|---|---|---|---|---|---|---|
| 1 |   |   |   | 99 | L | L | L | L | S |
| 2 |   |   |   | 98 | L | L | L | L | S |
| 3 |   |   |   | 97 | L | L | L | L | S |
| 4 |   |   |   | 96 | L | L | L | L | S |
| 5 |   |   |   | 95 | L | L | L | L | S |
| 6 |   |   |   | 94 | L | L | L | L | CL |
| 7 |   |   |   | 93 | L | L | L | L | CL |
| 8 |   |   |   | 92 | L | L | L | L | CL |
| 9 |   |   |   | 91 | L | L | L | L | CL |
| 10 |   |   |   | 90 | L | L | L | L | CL |
|   | 1 |   |   | 99 | L | L | L | L | S |
|   | 2 |   |   | 98 | L | L | L | L | S |
|   | 3 |   |   | 97 | L | L | L | L | S |
|   | 4 |   |   | 96 | L | L | L | L | S |
|   | 5 |   |   | 95 | L | L | L | L | S |
|   | 6 |   |   | 94 | L | L | L | L | S |
|   | 7 |   |   | 93 | L | L | L | L | S |
|   | 8 |   |   | 92 | L | L | L | L | S |
|   | 9 |   |   | 91 | L | L | L | L | S |
|   | 10 |   |   | 90 | L | L | L | L | S |
|   |   | 1 |   | 99 | L | L | L | L | S |
|   |   | 2 |   | 98 | L | L | L | L | S |
|   |   | 3 |   | 97 | L | L | L | S | S |
|   |   | 4 |   | 96 | L | L | L | S | S |
|   |   | 5 |   | 95 | L | L | L | S | S |
|   |   | 6 |   | 94 | L | L | L | S | S |
|   |   | 7 |   | 93 | L | L | L | S | S |
|   |   | 8 |   | 92 | L | L | CL | S | S |
|   |   | 9 |   | 91 | L | L | S | S | S |
|   |   | 10 |   | 90 | L | L | S | S | S |
|   |   |   | 1 | 99 | L | L | CL | S | S |
|   |   |   | 2 | 98 | L | CL | S | S | S |
|   |   |   | 3 | 97 | L | CL | S | S | S |
|   |   |   | 4 | 96 | L | CL | S | S | S |
|   |   |   | 5 | 95 | L | S | S | S | S |
|   |   |   | 6 | 94 | L | S | S | S | S |
|   |   |   | 7 | 93 | L | S | S | S | S |
|   |   |   | 8 | 92 | L | S | S | S | S |
|   |   |   | 9 | 91 | L | S | S | S | S |
|   |   |   | 10 | 90 | L | S | S | S | S |

Key:
L = liquid
S = solid
CL = cloudy liquid
RT = Room Temperature
C12ME = methyl dodecanoate
C14ME = methyl tetradecanoate
C16ME = methyl hexadecanoate
C18ME = methyl octadecanoate
C18:1ME = methyl octadecenoate to increase the levels of palmitoleic acid (16:1); (3) the activity of keto acyl-ACP synthase (KASII) is reduced by using gene repair oligonucleotide bases to introduce a stop codon in the coding sequence of the KASII gene; (4) the substrate specificity of the palmitoyl thioesterase (PTE) is altered to increase activity with capryloyl-ACP (C8), caproyl-ACP (C10), and lauroyl-ACP (C12) and in turn increase the levels of short and medium chain fatty acids by transforming the rapeseed plant with an *Cuphea* acyl-ACP thioesterase gene having short chain length specificity. The genetically modified rapeseed plant produces an oil having the following fatty acid composition: C8 accounts for about 5% of the oil; C10 accounts for about 5% of the oil; C12 accounts for about 15% of the oil; C16:1 and C18:1 together account for about 70% of the oil; and C14:0, C16:0, C18:0, C18:2 and C18:3 each account for less 1% of the oil. The methyl ester of the oil is liquid at approximately −20° C.

Unless otherwise defined, all technical and scientific terms used herein have the same meaning as commonly understood by one of ordinary skill in the art to which this invention belongs.

The inventions illustratively described herein may suitably be practiced in the absence of any element or elements, limitation or limitations, not specifically disclosed herein. Thus, for example, the terms "comprising," "including," "containing," etc. shall be read expansively and without limitation. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the invention claimed.

Thus, it should be understood that although the invention has been specifically disclosed by preferred embodiments and optional features, modification, improvement and variation of the inventions embodied therein herein disclosed may be resorted to by those skilled in the art, and that such modifications, improvements and variations are considered to be within the scope of this invention. The materials, methods, and examples provided here are representative of preferred embodiments, are exemplary, and are not intended as limitations on the scope of the invention.

The invention has been described broadly and generically herein. Each of the narrower species and subgeneric groupings falling within the generic disclosure also form part of the invention. This includes the generic description of the invention with a proviso or negative limitation removing any subject matter from the genus, regardless of whether or not the excised material is specifically recited herein.

In addition, where features or aspects of the invention are described in terms of Markush groups, those skilled in the art will recognize that the invention is also thereby described in terms of any individual member or subgroup of members of the Markush group.

All publications, patent applications, patents, and other references mentioned herein are expressly incorporated by reference in their entirety, to the same extent as if each were incorporated by reference individually. In case of conflict, the present specification, including definitions, will control.

That which is claimed is:

1. A mixture of fatty acids comprising:
   80% to 100% saturated fatty acids having 8-12 carbons and monounsaturated fatty acids having 12-18 carbons;
   5% to 80% caprylic acid (C8:0) and capric acid (C10:0), and
   6% to 20% lauric acid (C12:0);
   wherein said monounsaturated fatty acids account for 5% to 95% by weight of the mixture; and
   wherein said mixture comprises less than 20% polyunsaturated fatty acids and saturated fatty acids having more than 12 carbons; and
   wherein:
   (1) caprylic acid (C8:0), capric acid (C10:0), and lauric acid (C12:0) together account for 20% to 40% of the mixture;
   (2) oleic acid (C18:1) and palmitoleic acid (16:1) together account for 50% to 85% of the mixture;
   (3) stearic (18:0) and palmitic acid (16:0) account for less than 4% of the mixture;
   (4) myristic acid (14:0) accounts for less than 2% of the mixture;
   (5) linoleic acid (18:2) and linolenic acid (18:3) together account for less than 3% of the mixture; or
   (6) arachidic acid (C20:0), behenic acid (C22:0) and lignoceric acid (C24:0) account for less than 1% of the mixture.

2. The mixture of claim 1, wherein said mixture comprises:
   55% to 65% oleic acid (C18:1);
   5% to 15% lauric acid (C12:0);
   15% to 25% capric acid (C10:0); and
   5% to 15% caprylic acid (C8:0).

3. The mixture according to claim 1, wherein said mixture is suitable for use as feedstock for the production of a fuel in an internal combustion engine, a fuel additive, a functional fluid, a freezing point depressant, a biodiesel, an aviation fuel, a home heating oil, or a substitute for kerosene.

4. A blend of two or more oils or fatty acids comprising the mixture of claim 1, wherein said blend is formulated to provide a composition selected from the group consisting of a biodiesel, fuel in an internal combustion engine, a fuel additive, a functional fluid, a freezing point depressant, an aviation fuel, a home heating oil, or a substitute for kerosene.

5. The mixture according to claim 1, wherein said mixture has a melting point of less than or equal to −10° C.

6. The mixture according to claim 1, wherein the mixture has a cloud point of less than or equal to 0° C.

7. The mixture according to claim 1, wherein the mixture has a pour point of less than or equal to 0° C.

8. The mixture according to claim 1, wherein the mixture is an oil.

9. The mixture according to claim 1, wherein the mixture is a blend of at least two different oils.

10. The mixture according to claim 1, wherein said mixture is formulated as a biodiesel or a biodiesel blend.

11. An oil derived from a vegetable oil or an animal fat comprising the mixture of claim 1.

12. The oil according to claim 11, wherein said oil is derived from one or more selected from the group consisting of canola, rapeseed, palm oil, palm kernel, coconut, tucum, sunflower, safflower, *Cuphea*, olive, macadamia, babassu, castor, peanut, cotton, flaxseed, linseed, cohune, and jatropha.

* * * * *